United States Patent
Isab et al.

(10) Patent No.: US 10,385,072 B2
(45) Date of Patent: Aug. 20, 2019

(54) GOLD(III) COMPLEXES AS ANTICANCER AGENTS AND A METHOD OF TREATING CANCER

(71) Applicant: King Fahd University of Petroleum and Minerals, Dhahran (SA)

(72) Inventors: Anvar Husain Abdul Kadir Isab, Dhahran (SA); Muhammad Altaf, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/654,784

(22) Filed: Jul. 20, 2017

(65) Prior Publication Data

US 2019/0023721 A1 Jan. 24, 2019

(51) Int. Cl.
*C07F 1/00* (2006.01)

(52) U.S. Cl.
CPC ................... *C07F 1/005* (2013.01)

(58) Field of Classification Search
CPC ...................................... C07F 1/005
See application file for complete search history.

(56) References Cited

PUBLICATIONS

Ronconi et al. (Inorg. Chem. 2005, 44, 1867-1881).*
Kubinyi (3D QSAR in Drug Design: Ligand-Protein Interactions and Molecular Similarity, vol. 2-3, Springer, 1998, 800 pages). pp. 243-444 provided.*
Wermuth, The Practice of Medicinal Chemsitry, 2d ed. (2003), 768 pages. Chs. 9-10 provided.*
Muhammad Altaf et al., "New bipyridine gold (III) dithiocarbamate-containing complexes exerted a potent anticancer activity against cisplatin-resistant cancer cells independent of p53 status," Oncotarget, Nov. 18, 2016. vol. 8, No. 1, pp. 490-505.

* cited by examiner

*Primary Examiner* — Robert H Havlin
(74) *Attorney, Agent, or Firm* — Oblon, McClelland, Maier & Neustadt, L.L.P.

(57) ABSTRACT

Gold(III) complexes containing mixed ligands. A method of treating cancer with these complexes is disclosed. The complexes are cytotoxic to prostate, breast, ovarian, and Hodgkin lymphoma cancer cell lines. These complexes were either more potent than cisplatin or had similar potency to cisplatin.

12 Claims, 7 Drawing Sheets

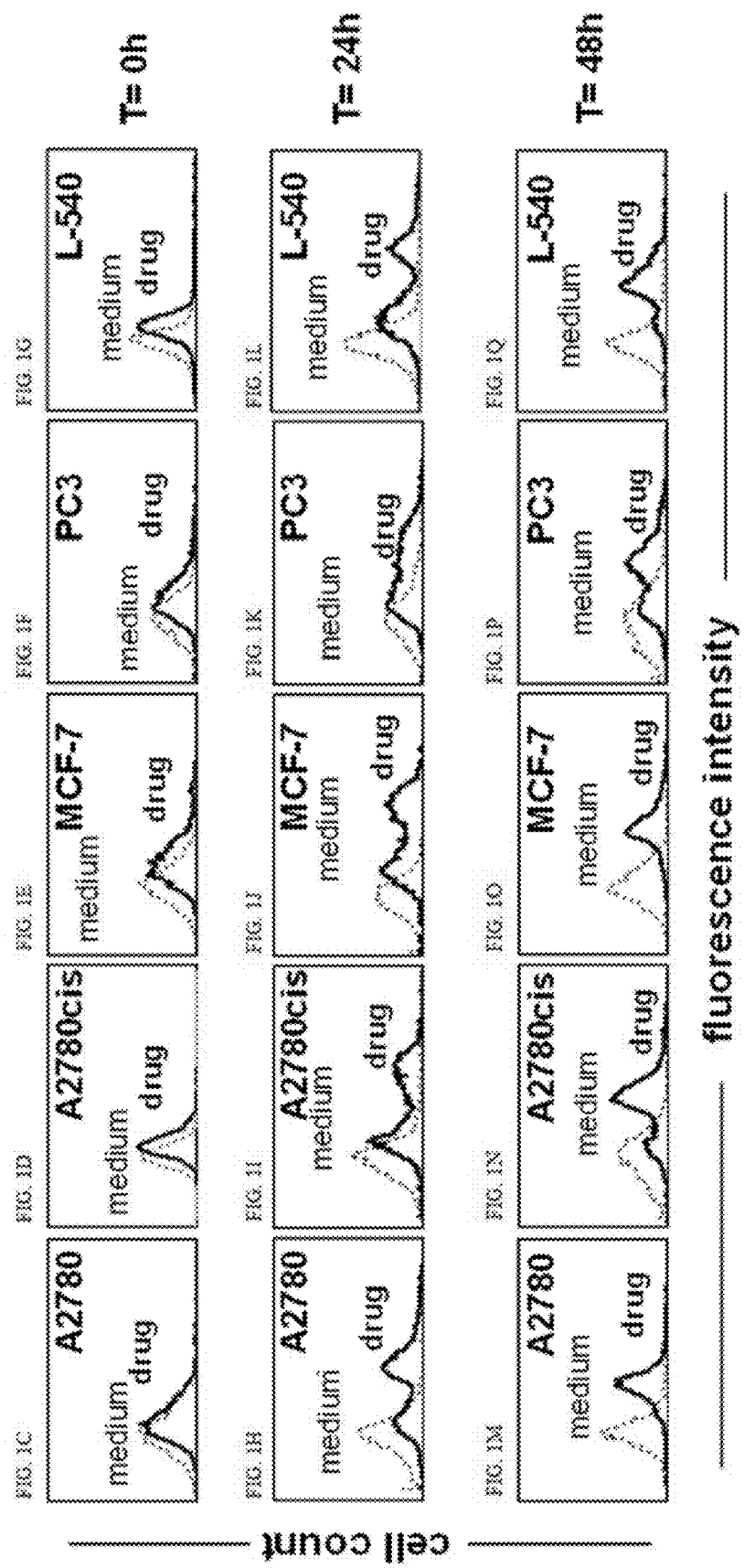

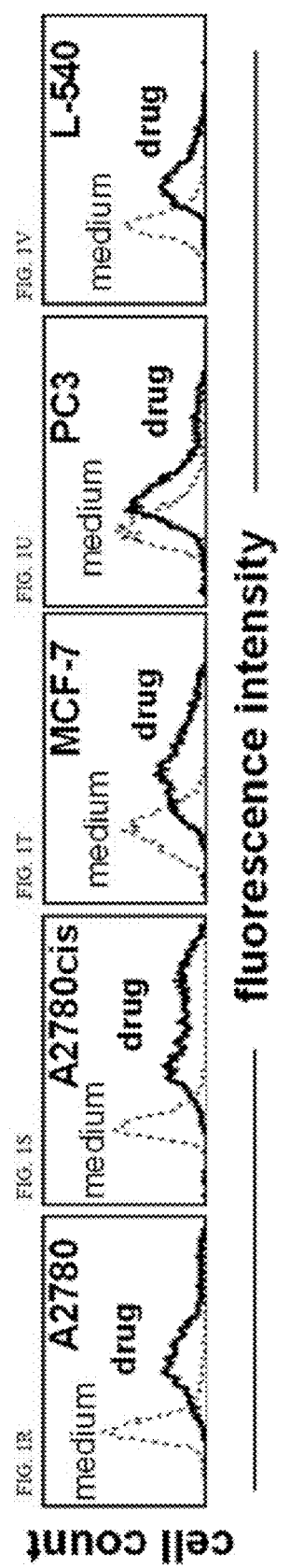

GOLD(III) COMPLEXES AS ANTICANCER AGENTS AND A METHOD OF TREATING CANCER

STATEMENT OF FUNDING ACKNOWLEDGEMENT

This project was funded by the National Plan for Science and Innovation (MARIFAH)-King Abdulaziz City for Science and Technology (KACST) through the Science and Technology Unit at King Fahd University of Petroleum and Minerals (KFUPM) of Saudi Arabia, award No. 14-MED64-04.

STATEMENT REGARDING PRIOR DISCLOSURES BY THE INVENTORS

Aspects of this technology are described in an article "New Bipyridine Gold(III) Dithiocarbamate-Containing Complexes Exerted A Potent Anticancer Activity Against Cisplatin-Resistant Cancer Cells Independent Of p53 Status" in Oncotarget, 2017, Vol. 8, (No. 1), pp. 490-505, published on Nov. 18, 2016, which is incorporated herein by reference in its entirety.

BACKGROUND OF THE DISCLOSURE

Technical Field

The present disclosure relates to gold(III) complexes with anticancer activity and a method of treating cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The discovery of the anticancer properties of cisplatin around 1965 attracted attention to the area of metal-based anticancer agents (Rosenberg, B.; Camp, L. V., Krigas, T. Inhibition of cell division in *Escherichia coli* by electrolysis products from a platinum electrode. *Nature.* 1965, 205, 698-699; and Rosenberg, B.; Camp, L. V.; Trosko J. E.; Mansour, V. H. Platinum compounds: a new class of potent antitumour agents. *Nature.* 1969, 222, 385-386, each incorporated herein by reference in their entirety). The anticancer effects of cisplatin suggested that platinum and non-platinum metal-based compounds, in principle, might be as valuable as organic anticancer drugs (Gabbiani, C.; Casini, A.; Messori, L. Gold(III) compounds as anticancer drugs. *Gold Bulletin.* 2007, 40, 73-81, incorporated herein by reference in its entirety). Cisplatin, cis-[Pt(NH$_3$)$_2$Cl$_2$], and a few related platinum compounds, such as carboplatin and oxaliplatin, are the most commonly used anticancer agents (Ronconi, L.; Fregona, D. The Midas touch in cancer chemotherapy: from platinum-to gold-dithiocarbamato complexes. *Dalton Trans.,* 2009, 10670-10680; and Abu-Surrah, A. S.; Kettunen, M. Platinum group antitumor chemistry: design and development of new anticancer drugs complementary to cisplatin. *Curr. Med. Chem.* 2006, 13, 1337-1357, each incorporated herein by reference in their entirety).

Presently, platinum drugs take on a significant role in the domain of the established medical treatments for cancer (Barnes, K. R.; Lippard, S. J. Cisplatin and related anticancer drugs: recent advances and insights. *Met. Ions Biol. Syst.,* 2004, 42, 143-177; Reedijk, J. New clues for platinum antitumor chemistry: kinetically controlled metal binding to DNA. *Proc. Natl. Acad. Sc. USA,* 2003, 100, 3611-3616; and Wang. D., Lippard. S. J. Cellular processing of platinum anticancer drugs. *Nat. Rev. Drug Discov.* 2005, 4, 307-320, each incorporated herein by reference in their entirety). The extensive clinical success of platinum compounds has triggered a great deal of awareness in other platinum and non-platinum metallodrugs that might demonstrate distinctly different cytotoxic properties, hopefully accompanied by a different prototype of anticancer specificities, particularly against cisplatin-resistant tumor cells, and by a more encouraging toxicological profile. Thus, in the span of three to four decades, a variety of metal compounds have been investigated as potential anticancer agents based on several non-platinum metals, for instance, ruthenium, palladium, titanium, gold, and copper etc. (Sigel, A.; Sigel, H.; *Metal ions in biological systems, Zinc and its role in biology and nutrition,* New York. 2004, 15; Sigel, A.; Sigel, H.; Metal ions in biological systems, New York. 2005; Jakupec, M. A.; Keppler, B. K. Gallium in cancer treatment. Metal ions in biological systems, New York. 2004; Bruijnincx, P. C. A.; Sadler, P. J. New trends for metal complexes with anticancer activity. *Curr. Opin. Chem. Biol.* 2008, 12, 197-206; Alessio E.; Mestroni G.; Bergamo A.; Sava G. Ruthenium antimetastatic agents. *Curr. Top Med. Chem.* 2004, 4, 1525-1535; and Ang, W. H.; Dyson, P. J. Classical and Non-Classical Ruthenium-Based Anticancer Drugs: Towards Targeted Chemotherapy. *Eur. J. Inorg. Chem.* 2006 4003-4018, each incorporated herein by reference in their entirety).

Therefore, it is an objective of this disclosure to provide gold(III) complexes with anticancer activity and a method for treating cancer.

BRIEF SUMMARY

A first aspect of the disclosure relates to a gold(III) complex selected from the group consisting of:

a gold(III) complex represented by formula (I), a salt thereof, a solvate thereof, a derivative thereof, and a prodrug thereof;

a gold(III) complex represented by formula (II), a salt thereof, a solvate thereof, a derivative thereof, and a prodrug thereof;

a gold(III) complex represented by formula (III), a salt thereof, a solvate thereof, a derivative thereof, and a prodrug thereof; and mixtures thereof;

wherein formulae (I), (II), and (III) are:

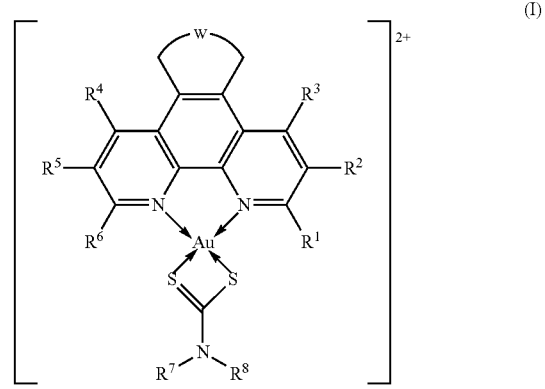

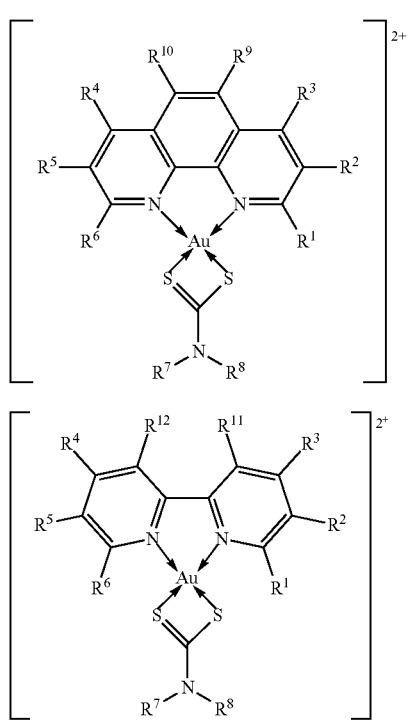

where $R^1$, $R^2$, $R^3$, $R^4$, $R^5$, $R^6$, $R^9$, $R^{10}$, $R^{11}$, and $R^{12}$ are independently selected from the group consisting of hydrogen, hydroxy, cyano, nitro, fluoro, chloro, bromo, iodo, an optionally substituted alkyl, an optionally substituted alkenyl, an optionally substituted alkynyl, an optionally substituted cycloalkyl, an optionally substituted aryl, an optionally substituted arylalkyl, an optionally substituted alkanoyl, and an optionally substituted aroyl;

$R^7$ and $R^8$ are independently selected from the group consisting of an optionally substituted alkyl, an optionally substituted cycloalkyl, an optionally substituted aryl, and an optionally substituted arylalkyl; and W is an optionally substituted arylene.

In one embodiment, the gold(III) complex is represented by formula (III), a salt thereof, a solvate thereof, a derivative thereof, or a prodrug thereof, and $R^1$, $R^2$, $R^3$, $R^4$, $R^5$, $R^6$, $R^{11}$, and $R^{12}$ are independently a hydrogen or an optionally substituted alkyl.

In one embodiment, $R^7$ and $R^8$ are independently an optionally substituted alkyl or an optionally substituted arylalkyl.

In one embodiment, the gold(III) complex further comprises a counterion which is at least one pharmaceutically acceptable anion selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

In one embodiment, $R^1$, $R^2$, $R^3$, $R^4$, $R^5$, $R^6$, $R^9$, $R^{10}$, $R^{11}$, and $R^{12}$ are independently a hydrogen or a methyl, and $R^7$ and $R^8$ are independently a methyl, an ethyl, or benzyl.

A second aspect of the disclosure relates to a pharmaceutical composition, comprising the gold(II) complex of the first aspect; and at least one pharmaceutically acceptable carrier and/or excipient.

In one embodiment, the at least one pharmaceutically acceptable carrier and/or excipient is selected from the group consisting of water, an organic solvent, an animal fat, a vegetable fat, a vegetable oil, and a polymer.

In one embodiment, the pharmaceutical composition comprises 0.1-10 wt % of the gold(III) complex, based on a total weight of the pharmaceutically acceptable composition.

In one embodiment, the gold(III) complex is represented by formula (III), a salt thereof, a solvate thereof, a derivative thereof, or a prodrug thereof, and $R^1$, $R^2$, $R^3$, $R^4$, $R^5$, $R^6$, $R^{11}$, and $R^{12}$ are independently a hydrogen or an optionally substituted alkyl.

In one embodiment, $R^7$ and $R^8$ are independently an optionally substituted alkyl or an optionally substituted arylalkyl.

In one embodiment, the gold(III) complex further comprises a counterion which is at least one pharmaceutically acceptable anion selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

In one embodiment, $R^1$, $R^2$, $R^3$, $R^4$, $R^5$, $R^6$, $R^9$, $R^{10}$, $R^{11}$, and $R^{12}$ are independently a hydrogen or a methyl, and $R^7$ and $R^8$ are independently a methyl, an ethyl, or benzyl.

A third aspect of the disclosure relates to a method for treating cancer, comprising administering an effective amount of the gold(III) complex of the first aspect to a subject in need thereof:

In one embodiment, the effective amount is in a range of 1-100 mg/kg body weight of the subject.

In one embodiment, the cancer is at least one selected from the group consisting of prostate cancer, lung cancer, breast cancer, ovarian cancer, and Hodgkin lymphoma.

In one embodiment, the cancer is prostate cancer which is resistant to androgen deprivation therapy.

In one embodiment, the cancer is resistant to at least one platinum-based chemotherapy drug.

In one embodiment, the cancer is ovarian cancer.

A fourth aspect of the disclosure relates to a method for inhibiting growth of cancer cells, comprising contacting a cytotoxic amount of the gold(III) complex of the first aspect with the cancer cells.

In one embodiment, the cancer cells are from at least one cell line selected from the group consisting of PC3, MCF-7, A2780, A2780cis, A2780CP-16, H460, A549, H226, H838, H157, H1975, H2122, SKLU1, H1299, and L-540.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1C is an overlay of the flow cytometry analyses of non-treated A2780 cells (medium) and A2780 cells before being treated with compound 1 (drug).

FIG. 1D is an overlay of the flow cytometry analyses of non-treated A2780cis cells (medium) and A2780cis cells before being treated with compound 1 (drug).

FIG. 1E is an overlay of the flow cytometry analyses of non-treated MCF-7 cells (medium) and MCF-7 cells before being treated with compound 1 (drug).

FIG. 1F is an overlay of the flow cytometry analyses of non-treated PC3 cells (medium) and PC3 cells before being treated with compound 1 (drug).

FIG. 1G is an overlay of the flow cytometry analyses of non-treated L-540 cells (medium) and L-540 cells before being treated with compound 1 (drug).

FIG. 1H is an overlay of the flow cytometry analyses of non-treated A2780 cells (medium) and A2780 cells treated with compound 1 at $IC_{75}$ for 24 hours (drug).

FIG. 1I is an overlay of the flow cytometry analyses of non-treated A2780cis cells (medium) and A2780cis cells before being treated with compound 1 at $IC_{75}$ for 24 hours (drug).

FIG. 1J is an overlay of the flow cytometry analyses of non-treated MCF-7 cells (medium) and MCF-7 cells before being treated with compound 1 at $IC_{75}$ for 24 hours (drug).

FIG. 1K is an overlay of the flow cytometry analyses of non-treated PC3 cells (medium) and PC3 cells before being treated with compound 1 at $IC_{75}$ for 24 hours (drug).

FIG. 1L is an overlay of the flow cytometry analyses of non-treated L-540 cells (medium) and L-540 cells before being treated with compound 1 at $IC_{75}$ for 24 hours (drug).

FIG. 1M is an overlay of the flow cytometry analyses of non-treated A2780 cells (medium) and A2780 cells treated with compound 1 at $IC_{75}$ for 48 hours (drug).

FIG. 1N is an overlay of the flow cytometry analyses of non-treated A2780cis cells (medium) and A2780cis cells before being treated with compound 1 at $IC_{75}$ for 48 hours (drug).

FIG. 1O is an overlay of the flow cytometry analyses of non-treated MCF-7 cells (medium) and MCF-7 cells before being treated with compound 1 at ICs for 48 hours (drug).

FIG. 1P is an overlay of the flow cytometry analyses of non-treated PC3 cells (medium) and PC3 cells before being treated with compound 1 at $IC_{75}$ for 48 hours (drug).

FIG. 1Q is an overlay of the flow cytometry analyses of non-treated L-540 cells (medium) and L-540 cells before being treated with compound 1 at $IC_{75}$ for 48 hours (drug).

FIG. 1R is an overlay of the flow cytometry analyses of non-treated A2780 cells (medium) and A2780 cells treated with compound 1 at $IC_{75}$ for 72 hours (drug).

FIG. 1S is an overlay of the flow cytometry analyses of non-treated A2780cis cells (medium) and A2780cis cells before being treated with compound 1 at $IC_{75}$ for 72 hours (drug).

FIG. 1T is an overlay of the flow cytometry analyses of non-treated MCF-7 cells (medium) and MCF-7 cells before being treated with compound 1 at $IC_{75}$ for 72 hours (drug).

FIG. 1U is an overlay of the flow cytometry analyses of non-treated PC3 cells (medium) and PC3 cells before being treated with compound 1 at ICs for 72 hours (drug).

FIG. 1V is an overlay of the flow cytometry analyses of non-treated L-540 cells (medium) and L-540 cells before being treated with compound 1 at $IC_{75}$ for 72 hours (drug).

DETAILED DESCRIPTION OF THE EMBODIMENTS

Figure 1A:
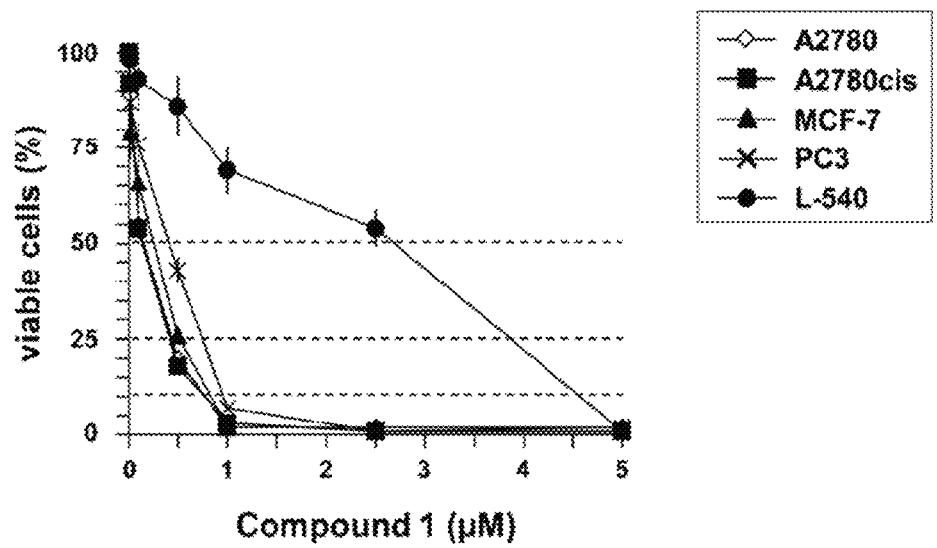
FIG. 1A shows the percentages of viable cancer cells after the cancer cells were in contact with compound 1 for 72 hours.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, "compound" and "complex" are used interchangeably, and are intended to refer to a chemical entity, whether in the solid, liquid or gaseous phase, and whether in a crude mixture or purified and isolated.

The phrase "pharmaceutically acceptable" as used herein refers to counterions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo or ex vivo.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity compared to the parent compound. Derivatization (i.e. modification) may involve substitution of one or more moieties within the molecule (e.g. a change in functional group). The term "derivative" also includes conjugates, and prodrugs of a parent compound (i.e. chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis (Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier Wang et al. (1999) Curr. Pharm. Design. 5(4):265-287; Pauletti et al. (1997). Adv. Drug. Delivery Rev. 27:235-256; Mizen et al. (1998) Pharm. Biotech. 11:345-365; Gaignault et al. (1996) Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Eur. J. Drug Metab. Pharmacokinet., 15(2): 143-53; Balimane and Sinko (1999) Adv. Drug Delivery Rev., 39(1-3):183-209; Browne (1997) Clin. Neuropharmacol. 20(1): 1-12; Bundgaard (1979) Arch. Pharm. Chemi. 86(1): 1-39; H. Bundgaard, ed. (1985) Design of Prodrugs, New York: Elsevier, Fleisher et al. (1996) Adv. Drug Delivery Rev. 19(2): 115-130; Fleisher et al. (1985) Methods Enzymol. 112: 360-81; Farquhar D, et al. (1983) J. Pharm. Sci., 72(3): 324-325; Han, H. K. et al. (2000) AAPS Pharm Sci., 2(1): E6; Sadzuka Y. (2000) Curr. Drug Metab. 1(1):31-48; D. M. Lambert (2000) Eur. J. Pharm. Sci., 11 Suppl 2:S15-27-each incorporated herein by reference in its entirety). In some embodiments, "pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. An example, without limitation, of a prodrug would be a compound of the present invention, which is, administered as an ester, phosphate, amide, carbamate, or urea.

As used herein, the term "analog" refers to a chemical compound that is structurally similar to a parent compound, but differs slightly in composition (e.g. at least one atom or functional group is different, added, or removed). The analog may or may not have different chemical or physical properties than the original compound and may or may not have improved biological and/or chemical activity. For example, the analog may be more hydrophilic or it may have altered reactivity compared to the parent compound. The analog may mimic the chemical and/or biological activity of the parent compound (i.e. it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

The term "solvate" means a physical association of the gold(III) complexes of formulae (I), (II), or (III) with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or non-stoichiometric amount of the solvent molecules. Solvate encompasses both solution-phase and isolable solvates. Exemplary solvates include, but are not limited to, hydrates, ethanolates, methanolates, and isoprpanolates. Methods of solvation are generally known in the art.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

It is known that gold(III) has a $d^8$ electronic configuration and the gold(III) complexes are usually square planar, similar to platinum(II) complexes. Despite the similarity, very little literature data exist on the use of gold(III) compounds as anticancer agents. This may be due to the high redox potential for gold(III) compounds. The gold(III) compounds may be relatively unstable thus hampering their application as the medicinal agents under normal physiological conditions (Pinto, H. M.; Schornagel J. H.; (Eds.), Platinum and Other Metal Coordination Compounds in Cancer Chemotherapy, Plenum, New York. 1996; Hambley, T. W. Platinum binding to DNA: structural controls and consequences. J. Chem. Soc., Dalton Trans. 2001, 19, 2711-2718; Lippert, (Ed.) Cisplatin-Chemistry and Biochemistry of a Leading Anticancer Drug. WIliey-VCH, Weinheim. 1999, each incorporated herein by reference in their entirety).

Since the beginning of the $21^{st}$ century, a series of gold(III) compounds were reported to be stable under physiological-like conditions and also exhibited appreciable in vitro cytotoxicity toward some human tumor cell lines. Such noticeable stability of gold(III) compounds re-attracted the research community to synthesize gold(III) compounds and evaluate their biological activity (Milacic V.; Fregona D.; Dou, Q. P. Gold complexes as prospective metal-based anticancer drugs. Histol Histopathol, 2008, 23, 101-108; and Casini, A.; Hartinger, C.; Gabbiani, C.; Mini, E.; Dyson, P. J.; Keppler, B. K.; Messori, L. Gold(III) compounds as anticancer agents: Relevance of gold-protein interactions for their mechanism of action. J. Inorg. Biochem. 2008, 102, 564-575, each incorporated herein by reference in their entirety). Parish et al. described the synthesis of stable gold(III) compounds using 2-(dimethylamino)methyl)phenyl as a ligand. Parish's gold(III) compounds are similar structurally to cisplatin (Parish R. V.; Howe B. P., Wright J. P.; Mack J.; Pritchard R. G.; Buckley R. G.; Elsome A M.; Fricker S. P. Chemical and biological studies of dichloro (2-((dimethylamino) methyl) phenyl) gold(III). *Inorg. Chem.* 1996 35, 1659-1666; and Parish, R. V.; Mack, J.; Hargreaves, L.; Wright, J. P.; Buckley, R. G.; Elsome, A. M.; Fricker, S. P.; Theobald B. R. C. Chemical and biological reactions of diacetato[2-(dimethylaminomethyl)-phenyl] gold(III), [Au(OCMe)$_2$(dmamp)]. *J. Chem. Soc., Dalton Trans.* 1996, 69-74, each incorporated herein by reference in their entirety). The acceptable solution stability of these gold(III) compounds allowed for extensive in vitro and in vivo pharmacological testing. As a result, other cytotoxic gold(III) compounds were synthesized by other research groups. The gold(III) compounds (e.g., gold(III) porphyrins) showed very striking biological trends (Giovagnini, L.; Ronconi, L.; Aldinucci, D.; Lorenzon, D.; Sitran, S.; Fregona D. Synthesis, characterization, and comparative in vitro cytotoxicity studies of platinum (I), palladium (II), and gold(III) methylsarcosinedithiocarbamate complexes. *J. Med. Chem.*, 2005, 48, 1588-1595; and Che, C. M.; Sun, R. W.; Yu. W. Y.; Ko, C. B.; Zhu, N. Y.; Sun, H. Z. Gold(III) porphyrins as a new class of anticancer drugs: cytotoxicity, DNA binding and induction of apoptosis in human cervix epitheloid cancer cells. *Chem Commun.* 2003, 14, 1718-1719; Milovanović, M.; Djeković, A.; Volarević, V.; Petrović, B.; Arsenijević, N.; Bugarčić, . D. Ligand substitution reactions and cytotoxic properties of [Au(L)Cl$_2$]$^+$ and [AuCl$_2$(DMSO)$_2$]$^+$ complexes (L=ethylenediamine and S-methyl-1-cysteine). *J. Inorg. Biochem.* 2010, 104, 944-949; Ronconi, L.; Giovagnini, L.; Marzano, C.; Bettio, F.; Graziani, R.; Pilloni, G.; Fregona, D. Gold dithiocarbamate derivatives as potential antineoplastic agents: design, spectroscopic properties, and in vitro antitumor activity. *Inorg. Chem.*, 2005, 44, 1867-1881; and Tiekink, E. R. T. Gold derivatives for the treatment of cancer. *Crit. Rev. Oncol. Hematol.* 2002, 42, 225-248; Tiekink, E. R. T. Anticancer potential of gold complexes. *Inflammopharmacology.* 2008, 16, 138-142; Ott, I. On the medicinal chemistry of gold complexes as anticancer drugs. *Coord. Chem. Rev.* 2009, 253, 1670-1681; Sun, R. W. Y.; Che, C. M. The anticancer properties of gold(III) compounds with dianionic porphyrin and tetradentate ligands. *Coord. Chem. Rev.* 2009, 253, 1682-1691; and Berners-Price, S. J.; Girard, G. R.; Hill, D. T.; Sutton, B. M.; Jarrett, P. S.; Faucette, L. F.; Johnson, R. K.; Mirabelli, C. K.; Sadler, P. J. Cytotoxicity and antitumor activity of some tetrahedral bis(diphosphino)gold(I) chelates. *J. Med. Chem.* 1990, 33, 1386-1392; Wang. Y.; He, Q. Y.; Sun, R. W.; Che, C. M.; Chiu, J. F. Gold(III) porphyrin 1a induced apoptosis by mitochondrial death pathways related to reactive oxygen species. *Cancer Res.*, 2005, 65, 11553-11564; Milacic V.; Chen D.; Ronconi L.; Landis-Piwowar K. R.; Fregona D.; Dou Q. P. A Novel Anticancer Gold(III) Dithiocarbamate Compound Inhibits the Activity of a Purified 20S Proteasome and 26S Proteasome in Human Breast Cancer Cell Cultures and Xenografts. *Cancer Res.* 2006, 66, 10478-10486; Wang, Y.; He, Q. Y.; Che, C. M.; Tsao, S. W.; Sun, R. W.; Chiu, J. F.; Modulation of gold(III) porphyrin 1a-induced apoptosis by mitogen-activated protein kinase signaling pathways. Biochem. Pharmacol. 2008, 75, 1282-1291; Messori, L.; Abbate, F.; Marcon, G.; Orioli, P.; Fontani, M.; Mini, E.; Mazzei, T.; Carotti, S.; O'Connell T.; Zanello, P. Gold(III) complexes as potential antitumor agents: solution chemistry and cytotoxic properties of some selected gold(III) compounds. *J. Med. Chem.* 2000, 43, 3541-3548; and Marcon, G.; Carotti, S.; Coronnello, M.; Messori, L.; Mini, E.; Orioli, P.; Mazzei, T.; Cinellu M. A.; Minghetti, G. Gold(III) complexes with bipyridyl ligands: solution chemistry, cytotoxicity, and DNA binding properties. *J. Med. Chem.* 2002, 45, 1672-1677; Abbate, F.; Orioli, P.; Bruno, B.; Marcon, G.; Messori, L. Crystal structure and solution chemistry of the cytotoxic complex 1,2-dichloro (o-phenanthroline) gold(III) chloride. *Inorg. Chim Acta.* 2000, 311, 1-5; Coronnello, M.; Mini, E.; Caciagli, B.; Cinellu, M. A.; Bindoli A.; Gabbiani, C.; Messori, L. Mechanisms of cytotoxicity of selected organogold(III) compounds. *J. Med. Chem.* 2005, 48, 6761-6765; Casini, A.; Cinellu, M. A.; Minghetti, G.; Gabbiani, C.; Coronnello, M.; Mini E.; Messori, L. Structural and solution chemistry, antiproliferative effects, and DNA and protein binding properties of a series of dinuclear gold(II) compounds with bipyridyl ligands. *J. Med. Chem.* 2006, 49, 5524-5531; Milacic. V.; Chen, D.; Ronconi, L.; Landis-Piwowar, K. R.; Fregona, D.; Don, Q. P. A Novel Anticancer Gold(III) Dithiocarbamate Compound Inhibits the Activity of a Purified 20S Proteasome and 26S Proteasome in Human Breast Cancer Cell Cultures and Xenografts. *Cancer Res.* 2006, 66, 10478-86; Casini, A.; Kelter, G.; Gabbiani, C.; Cinellu, M. A.; Minghetti, G.; Fregona, D.; Fiebig, H. H.; Messori, L Chemistry, antiproliferative properties, tumor selectivity, and molecular mechanisms of novel gold(III) compounds for cancer treatment: a systematic study. *J. Biol. Inorg. Chen.* 2009, 14, 1139-1149; and Aldinucci, D.; Ronconi, L.; Fregona, D. Groundbreaking gold(III) anticancer agents. *Drug Discov. Today.* 2009, 14, 1075-80; Akmadullina, N. S.; Churakov, A. V.; Retivov, V. M.; Sandu, R. A.; Shishilov, O. N. Gold(III) chloride and acetate complexes with bipyridine and phenanthroline. *Russian Journal of Coordination Russian.* 2012, 38, 589-595; Casini, A.; Celine, M. D.; Scopelliti, R.; Zakeeruddin, S. M.; Gratzel, M.; Dyson, P. J. Synthesis, characterization and biological properties of gold (III) compounds with modified bipyridine and bipyridylamine ligands. *Dalton Trans.*, 2010, 39, 2239-2245; Ogawa, T.; Sakamoto, M.; Honda, H.; Matsumoto, T.; Kobayashi, A.; Kato, M.; Chang, H. Self-association and columnar liquid crystalline phase of cationic alkyl-substituted-bipyridine benzenedithiolato gold(III) complexes. *Dalton Trans.* 2013, 42, 5995-16005, each incorporated herein by reference in their entirety).

An aspect of the disclosure relates to a gold(III) complex represented by formula (I), a salt thereof, a solvate thereof, a derivative thereof, and a prodrug thereof; a gold(III) complex represented by formula (II), a salt thereof, a solvate thereof, a derivative thereof, and a prodrug thereof; and a gold(III) complex represented by formula (III), a salt thereof, a solvate thereof, a derivative thereof, and a prodrug thereof.

Formulae (I), (II), and (III) are:

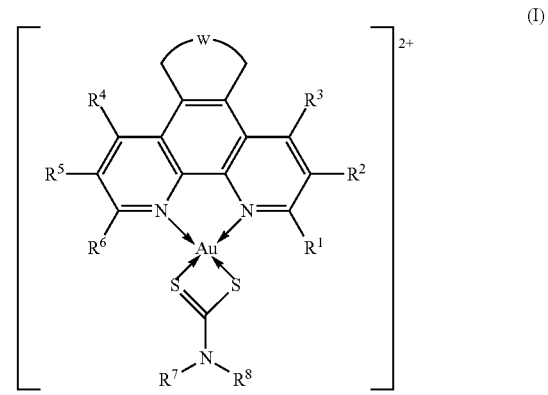

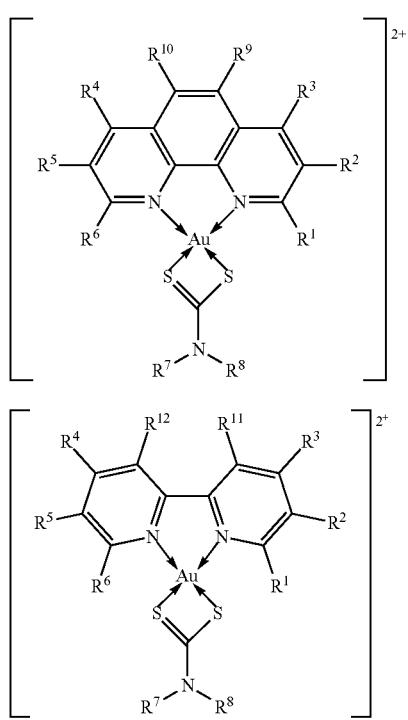

where $R^1$, $R^2$, $R^3$, $R^4$, $R^5$, $R^6$, $R^9$, $R^{10}$, $R^{11}$ and $R^{12}$ are independently selected from the group consisting of hydrogen, hydroxy, cyano, nitro, fluoro, chloro, bromo, iodo, an optionally substituted alkyl, an optionally substituted alkenyl, an optionally substituted alkynyl, an optionally substituted cycloalkyl, an optionally substituted aryl, an optionally substituted arylalkyl, an optionally substituted alkanoyl, and an optionally substituted aroyl;

$R^7$ and $R^8$ are independently selected from the group consisting of an optionally substituted alkyl, an optionally substituted cycloalkyl, an optionally substituted aryl, and an optionally substituted arylalkyl; and W is an optionally substituted arylene.

The term "alkyl", as used herein, unless otherwise specified, refers to a straight or branched hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, 1-methylcyclopropyl and 2-methycyclopropyl groups, are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "alkynyl" refers to a straight or branched hydrocarbon fragment containing at least one C≡C triple bond. Exemplary alkynyl groups include, without limitation, ethynyl, 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, and 9-decynyl.

The term "aryl", as used herein, and unless otherwise specified, refers to phenyl, biphenyl, naphthyl, anthracenyl, and the like.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl.

Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The substituent "W" is an optionally substituted arylene, which is a substituent derived from an arene that has had a hydrogen atom removed from each of two adjacent ring carbon atoms. Exemplary arenes include an optionally substituted benzene, naphthalene, anthracene, phenanthrene, tetracene, chrysene, triphenylene, pyrene, pentacene, benzo[a]pyrene, corannulene, benzo[ghi]perylene, coronene, ovalene, benzo[c]fluorene. In some embodiments, the arylene is a phenylene.

As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined herein); halogen (e.g. chlorine, bromine, fluorine or iodine); alkoxy (i.e. straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3- dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl); hydrocarbyl; arylalkyl; hydroxy; alkoxy; oxo; alkanoyl; alkanoyloxy; amino; alkylamino; arylamino; arylalkylamino; disubstituted amines (e.g. in which the two amino substituents are selected from the exemplary group including, but not limited to, alkyl, aryl, or arylalkyl); alkanoylamino; thiol; alkylthio; arylthio; arylalkylthio; alkylthiono; arylthiono; arylalkylthiono; alkylsulfonyl; arylsulfonyl; arylalkylsulfonyl; sulfonamido (e.g. —SO$_2$NH$_2$); substituted sulfonamide; nitro; cyano; carboxy carbamyl (e.g. —CONH$_2$, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, and octylthio.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above and a carbonyl group (such as an ester, an acid chloride, a ketone, and an aldehyde) attached to the ring. Heteroarylcarbonyl groups include, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

Vinyl refers to an unsaturated substituent having at least one unsaturated double bond and having the formula CH$_2$=CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

In some embodiments, $R^1$, $R^2$, $R^3$, $R^4$, $R^5$, $R^6$, $R^9$, $R^{10}$, $R^{11}$, and $R^{12}$ are independently a hydrogen or an optionally substituted alkyl (e.g., methyl). In some embodiments, $R^7$ and $R^8$ are independently an optionally substituted alkyl or an optionally substituted arylalkyl. For example, $R^7$ and $R^8$ are independently a methyl, an ethyl, or benzyl.

In one embodiment, $R^1$ and $R^6$ are methyls, $R^2$, $R^3$, $R^4$, $R^5$, $R^9$, $R^{10}$, $R^{11}$, and $R^{12}$ are hydrogens, and $R^7$ and $R^8$ are independently a methyl, an ethyl, or benzyl. In some embodiments, $R^2$ and $R^5$ are methyls, $R^1$, $R^3$, $R^4$, $R^6$, $R^9$, $R^{10}$, $R^{11}$, and $R^{12}$ are hydrogens, and $R^7$ and $R^8$ are independently a methyl, an ethyl, or benzyl.

In some embodiments, the gold(III) complex may be in a form of a salt which includes a counterion. The counterion may be at least one pharmaceutically acceptable anion such as fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate. In some embodiments, the counterion is a halide, preferably a chloride.

In the gold(III) complexes of formulae (I), (II), and (III), the gold(III) atom may be covalently coordinated to the two pyridyl nitrogen atoms and the two sulfur atoms in the dithiocarbamato ligand. The two multidentate ligands may improve the chemical stability of the gold(III) atom. Further, the inclusion of dithiocarbamato ligand may reduce therapy-induced toxicity (e.g. nephrotoxicity) without compromising the efficacy of the gold(III) complex(es). In some embodiments, the gold(III) complex has one of the following structures:

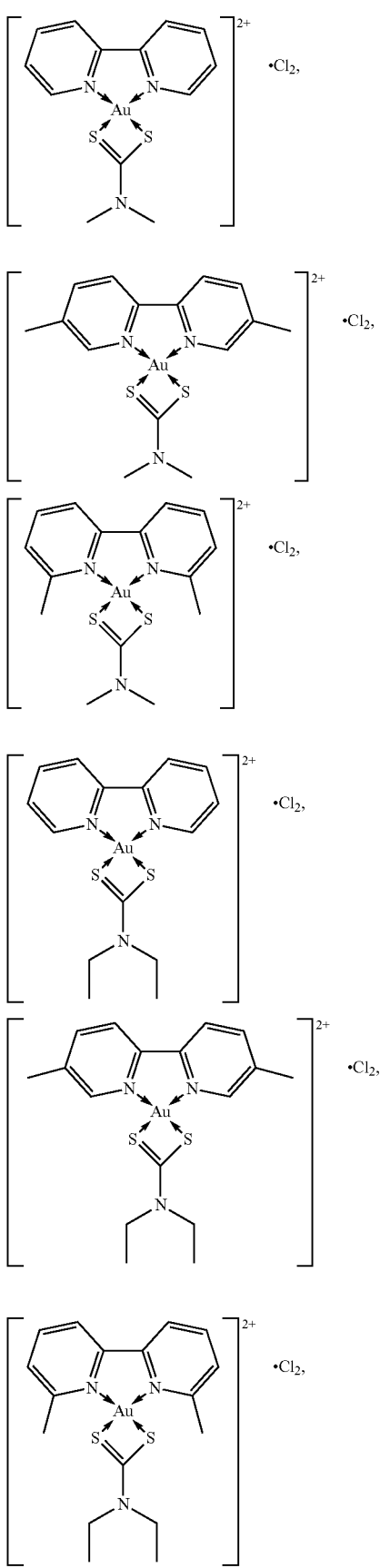
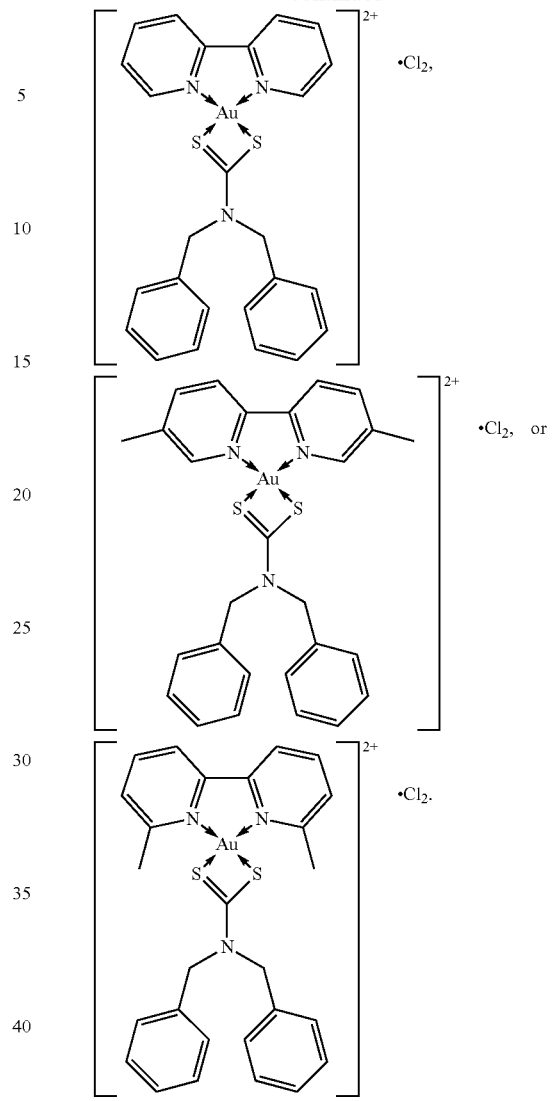
An aspect of the disclosure relates to a method of making the presently disclosed gold(III) complexes. A gold(III) precursor may be mixed with a dithiocarbamate salt and the following ligands thereby forming the respective gold(III) complexes of formulae (I), (II), and (III). The ligands are:
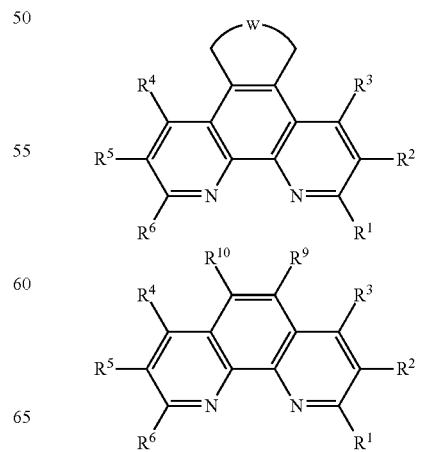

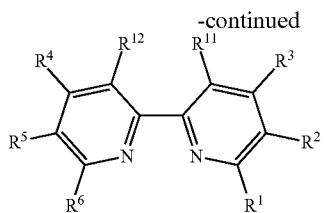

In some embodiments, the ligand may be 2,2'-bipyridine, 6,6'-dimethyl-2,2'-dipyridyl, 6-methyl-2,2'-dipyridyl, 4,4'-dimethyl-2,2'-dipyridyl, 5,5'-dimethyl-2,2'-dipyridyl, 4-4'-dimethoxy-2-2'-bipyridine, 4,4'-di-tert-butyl-2,2'-dipyridyl, 6,6'-dibromo-2,2'-dipyridyl, 6-bromo-2,2'-bipyridine, 2,2'-bipyridine-3,3'-diol, 4,4'-dinonyl-2,2'-dipyridyl, 4,4'-diphenyl-2,2'-dipyridyl, 5,5'-bis(trifluoromethyl)-2,2'-bipyridine, 1,10-phenanthroline, 1,10-phenanthrolin-5-amine, 5-chloro-1,10-phenanthroline, 4,7-dichloro-1,10-phenanthroline, 4,7-dihydroxy-1,10-phenanthroline, 5-methyl-1,10-phenanthroline, neocuproine, 4-methyl-1,10-phenanthroline, 5,6-dimethyl-1,10-phenanthroline, 5-nitro-1,10-phenanthroline, 3,4,7,8-tetramethyl-1,10-phenanthroline, pyrazino[2,3-f][1,10]phenanthroline, 4,7-dimethoxy-1,10-phenanthroline, 2-bromo-1,10-phenanthroline, 3,5,6,8-tetrabromo-1,10-phenanthroline, bathophenanthroline, and 2,9-dimethyl-4,7-diphenyl-1,10-phenanthroline.

The dithiocarbamate salt may be represented by the following formula:

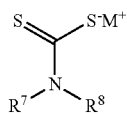

where $M^+$ is an alkali metal cation (e.g. sodium, potassium, cesium, lithium, and rubidium), ammonium, an optionally substituted alkylammonium, an optionally substituted arylammonium, or an optionally substituted alkylarylammonium. Exemplary dithiocarbamate salts include, without limitation, sodium dimethyldithiocarbamate, potassium dimethyldithiocarbamate, sodium diethyldithiocarbamate, potassium diethyldithiocarbamate, sodium dibenzyldithiocarbamate, potassium dibenzyldithiocarbamate, and hydrates thereof.

Exemplary gold(III) precursors include, without limitation, sodium tetrachloroaurate(III), potassium tetrachloroaurate(III), cesium tetrachloroaurate(III), sodium tetrabromoaurate(III), potassium tetrabromoaurate(III), caesium tetrabromoaurate(III), and hydrates thereof.

The gold(III) precursor and the ligand may be mixed with an alcohol to form a mixture. A concentration of the gold(III) precursor in the mixture may be in a range of 0.01-1 M, 0.02-0.5 M, or 0.025-0.3 M. A concentration of the ligand in the mixture may be in a range of 0.01-1 M, 0.02-0.5 M, or 0.025-0.3 M. A mole ratio of the gold(III) precursor to the ligand may be in a range of 0.9:1 to 1.5:1, 0.95:1 to 1.2:1, or 0.99:1 to 1.01:1. The mixture may be agitated for 0.5-10 hours, 1-6 hours, or 2-3 hours. After which, an aqueous solution of the dithiocarbamate salt may be mixed with the mixture to form a reaction mixture. A concentration of the dithiocarbamate salt in the aqueous solution may be in a range of 0.01-1 M, 0.02-0.5 M, or 0.05-0.3 M. A mole ratio of the gold(III) precursor to the dithiocarbamate salt may be in a range of 0.9:1 to 1.5:1, 0.95:1 to 1.2:1, or 0.99:1 to 1.01:1. The reaction mixture may be agitated for 0.1-10 hours, 0.5-6 hours, or 1-3 hours.

Precipitation/crystallization of the gold(II) complex of formulae (I), (II), or (III) may occur and the precipitate/crystals may be collected using methods known to those skilled in the art such as filtration.

Methods of agitating the mixture and/or the reaction mixture include, without limitation, using an agitator, a vortexer, a rotary shaker, a magnetic stirrer, a centrifugal mixer, or an overhead stirrer. In another embodiment, the mixture and/or the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm, even though it can also be mixed with a spatula. In one embodiment, the mixture and/or the reaction mixture is sonicated in an ultrasonic bath or with an ultrasonic probe.

As used herein, the term "solvent" includes, but is not limited to, water (e.g. tap water, distilled water, doubly distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof. Preferably, the solvent is absolute ethanol.

Another aspect of the disclosure relates to pharmaceutically acceptable composition containing the presently disclosed gold(III) complex(es) and a pharmaceutically acceptable carrier/excipient.

As used herein, a "composition" refers to a mixture of the active ingredient with other chemical components, such as pharmaceutically acceptable carriers and excipients. One purpose of a composition is to facilitate administration of the gold(III) complex(es) to a subject. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, a gold(II) complex represented by formula (I), a salt thereof, a solvate thereof, a derivative thereof, and a prodrug thereof; a gold(III) complex represented by formula (II), a salt thereof, a solvate thereof, a derivative thereof, and a prodrug thereof; and a gold(III) complex represented by formula (III), a salt thereof, a solvate thereof, a derivative thereof, and a prodrug thereof, any mixtures of the gold (111) complexes.

In most embodiments, the composition comprises at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the gold(III) complex(es). The composition may comprise 0.01-50 μM, 0.01-30 μM, preferably 0.01-10 μM of the gold(III) complex(es). In some embodiments, the composition comprises up to 0.1 wt %, 1 wt %, 5 wt %, or 10 wt % of the pharmaceutically acceptable salt of the gold(III) complex of formulae (I), (II), and/or (III). In some embodiments, the composition comprises up to 0.1 wt %, 1 wt %, 5 wt %, or 10 wt % of the pharmaceutically acceptable solvate of the gold(III) complex of formulae (I), (II), and/or (III). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In one embodiment, the composition further comprises a second active ingredient, such as an anticancer agent, for the treatment or prevention of neoplasm, of tumor or cancer cell division, growth, proliferation and/or metastasis in the subject; induction of death or apoptosis of tumor and/or cancer cells; and/or any other form of proliferative disorder.

The anticancer agent is at least one of a mitotic inhibitor; an alkylating agent; an antimetabolite; a cell cycle inhibitor; an enzyme, a topoisomerase inhibitor such as CAMP-TOSAR (irinotecan); a biological response modifier; an anti-hormone; an antiangiogenic agent such as MMP-2, MMP-9 and COX-2 inhibitor, an anti-androgen; a platinum coordination complex (cisplatin, oxaliplatin, carboplatin); a substituted urea such as hydroxyurea; methylhydrazine derivative, e.g., procarbazine; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Examples of alkylating agents include, without limitation, fluorouracil (5-FU) alone or in further combination with leukovorin; other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite anticancer agents include, without limitation, folic acid analogs, e.g., methotrexate (used in the treatment of acute lymphocytic leukemia, choriocarcinoma, mycosis fungoides, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based anticancer agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic anticancer agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic anticancer agents such as L-asparaginase.

Examples of useful COX-II inhibitors include Vioxx, CELEBREX (celecoxib), valdecoxib, paracoxib, rofecoxib, and COX 189.

Some examples of MMP inhibitors useful are AG-3340, RO 32-3555, RS 13-0830, and compounds such as 3-[[4-(4-fluorophenoxy)-benzenesulfonyl]-(1-hydroxycarbamoyl-cyclopentyl)-amino]-propionic acid; 3-exo-3-[4-(4-fluorophenoxy)-benzenesulfonylamino]-8-oxa-bicyclo[3.2.1] octane-3-carboxylic acid hydroxyamide; (2R,3R) 1-[4-(2-chloro-4-fluoro-benzyloxy)-benzenesulfonyl]-3-hydroxy-3-methylpiperidine-2-carboxylic acid hydroxyamide; 4-[4-(4-fluorophenoxy)-benzenesulfonylamino]-tetrahydro-pyran-4-carboxylic acid hydroxyamide; 3-[[4-(4-fluoro-phenoxy) benzenesulfonyl]-(1-hydroxycarbamoyl-cyclobutyl)-amino]-propionic acid; 4-[4-(4-chloro-phenoxy) benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoy 1-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluorophenoxy)-benzenesulfonylamino]-8-oxa-bicyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

The composition may comprise other anticancer agents, including, but not limited to, agents capable of enhancing antitumor immune responses, such as CTLA4 (cytotoxic lymphocite antigen 4) antibodies, other agents capable of blocking CTLA4, trastuzumab, cetuximab, panitumumab, rituximab, bevacizumab, mapatumumab, conatumumab, and lexatumumab.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In some embodiments, the pharmaceutically acceptable carrier and/or excipient may be an organic solvent, a synthetic polymer, a fatty acid, a synthetic fatty ester, a vegetable oil, and/or a surfactant.

Exemplary organic solvents include, without limitation, the organic solvents and organic acids described herein in addition to glycol ethers (e.g. 1,2-dimethoxyethane, diglyme, triglyme), alkyl methyl sulfoxide (e.g., dimethyl sulfoxide, decylmethyl sulfoxide, tetradecylmethyl sulfoxide), ketone (e.g., acetone, butanone), esters (e.g. ethyl acetate, propyl acetate), an amide/lactam (e.g. dimethylformamide, dimethylacetamide, pyrrolidone, N-methyl-2-pyrrolidone, N-(2-hydroxyethyl) pyrrolidone), acetonitrile, propionitrile, butyronitrile, benzonitrile, ethylene carbonate, propylene carbonate, 1,3-dimethyl-3,4,5,6-tetrahydro-2(1H)-pyrimidinone, and mixtures thereof.

Exemplary synthetic polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (maleic anhydride), a polyvinyl alcohols, and copolymers, terpolymers, or combinations or mixtures therein. The copolymer/terpolymer may be a random copolymer/terpolymer, or a block copolymer/terpolymer.

The polylactide may be a polymerization product of L-lactide, D-lactide, or mixtures thereof. The tacticity of the polylactide polymer may be syndiotactic, atactic, or preferably, isotactic. As used herein, the term "tacticity" refers to the relative orientation of each methyl group in a repeating unit of polylactide polymer relative to the methyl groups in neighboring monomer units. In isotactic polylactide all the methyls are located on the same side of the polymer backbone. In syndiotactic polylactide, the methyls have alternate positions along the chain. In atactic polylactide, the methyls are placed randomly along the chain. Tacticity may be measured directly using proton or carbon-13 NMR, x-ray powder diffraction, secondary ion mass spectrometry (SIMS), vibrational spectroscopy (FTIR) and especially two-dimensional techniques. Tacticity may also be inferred by measuring another physical property, such as melting temperature, when the relationship between tacticity and that property is well-established.

Lactic acid-based polymers, and copolymers of lactic acid and glycolic acid (PLGA), including poly(D,L-lactide-co-glycolide) and poly(L-lactide-co-glycolide) may be preferred. In some embodiments, the PLGA polymers have a weight average molecular weights of between about 2,000 to about 100,000 and monomer ratios of lactic acid to glycolic acid of between about 50:50 to about 100:0.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide. A particular polyoxyethylene sorbitan fatty ester is polyoxyethylene 20 sorbitan monooleate also known as polysorbate 80 or Tween 80 (T80).

Surfactants may act as detergents, wetting agents, emulsifiers, foaming agents, and dispersants. Surfactants that can be present in the disclosed compositions include anionic surfactants, amphoteric surfactants, cationic surfactants, zwitterionic surfactants, non-ionic surfactants, and combinations thereof. Surfactants suitable for use in the present invention may include TWEEN®, polyethylene glycol (PEG), PLURONICS™, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, nonoxynol 30, and polysorbates such as polysorbate 20, polysorbate 40, polysorbate 60 or polysorbate 80.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker. New York, N.Y., 1980, which is incorporated herein by reference in its entirety).

An aspect of the disclosure relates to a method of treating cancer by administering an effective amount of the gold(III) complex disclosed herein (either alone or in combination with another gold(III) complex) to a subject in need thereof.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting ovarian cancer. White women or a person with (i) certain inherited genes (e.g. mutated BRCA1, BRCA2, ATM, TP53, CHEK2, PTEN, CDHI, STK11, and PALB2), (ii) radiation to one's chest, and/or (iii) exposure to diethylstilbestrol (DES), are at a higher risk of contracting breast cancer. People who have had infectious mononucleosis (an infection caused by the Epstein-Barr virus (EBV)), and/or are infected with HIV (human immunodeficiency virus) are at a higher risk of contracting Hodgkin lymphoma. People who smoke or regularly breathe in secondhand smoke, and/or exposed to carcinogens such as asbestos, radioactive substances (e.g., uranium, radon), inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer. African-American men and Caribbean men of African ancestry are at a higher risk of contracting prostate cancer. Also, men who have certain inherited genes (e.g. mutated BRCA1 and/or mutated BRCA2), and/or older than 50 are at a higher risk of contracting prostate cancer.

In another embodiment, the subject refers to a cancer patient who has been previously administered/treated with cisplatin and have cisplatin resistance (for example in the form of high ERCC1 mRNA levels, overexpression of HER-2/neu, activation of the PI3-K/Akt pathway, loss of p53 function, and/or overexpression of antiapoptotic bcl-2). In some embodiments, the subject refers to a cancer patient (e.g., a prostate cancer patient) who has been previously administered/treated with androgen deprivation therapy and have developed resistance to the therapy (for example in the form of recurring symptoms, a rise in prostate-specific antigen levels, and/or a progression of the tumor). As used herein, the term "androgen deprivation therapy" is an anti-hormone therapy for treating prostate cancer. Prostate cancer cells usually require androgen hormones, such as testosterone, to grow. Androgen deprivation therapy reduces the levels of androgen hormones, with drugs or surgery, to prevent the prostate cancer cells from growing.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include but are not limited to CT scan, MRI, DCE-MRI and PET scan.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the gold(III) complex(es) disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. In some embodiments, the effective amount may be in a range of 1-100 mg/kg based on the weight of the subject, preferably 10-80 mg/kg, more preferably 20-50 mg/kg.

The neoplastic activity of the tumor or cancer cells may be localized or initiated in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system. Preferably, the presently disclosed gold(III) complexes may be used to treat prostate cancer, lung cancer, breast cancer, ovarian cancer, and Hodgkin lymphoma such as classical Hodgkin lymphoma and nodular lymphocyte-predominant Hodgkin lymphoma. In some embodiments, the gold(III) complexes may be used to treat cisplatin-resistant ovarian cancer, androgen-resistant prostate cancer, and/or classical Hodgkin lymphoma. In one embodiment, the subject has ovarian cancer and is currently undergoing, or has completed a cisplatin-based chemotherapy regimen. In another embodiment, the subject has prostate cancer and is currently undergoing, or has completed an androgen-based chemotherapy regimen.

In treating certain cancers, the best approach is a combination of surgery, radiotherapy, and/or chemotherapy. Therefore, in at least one embodiment, the gold(III) complex (either alone or in combination) is employed with radiotherapy. In another embodiment, the gold(III) complex is employed with surgery. The radiotherapy and/or surgery may be before or after the composition is administered.

The gold(III) complex(es) may be administered in a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the gold(III) complex(es) and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between.

In certain embodiments, the gold(II) complex(es) and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In most embodiments, the method further comprises measuring a concentration of a biomarker and/or detecting a mutation in a biomarker before and/or after the composition or the gold(II) complex(es) is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary cancer biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin Dl, cyclin E, and ERβ. Exemplary cancer biomarkers for ovarian cancer and/or Hodgkin lymphoma include, without limitation, BRCA1, BRCA2, CCL17, CD163, CD30, NF-κB, Gal-1, CA125, HE4, mesothelin, transthyretin, ApoA1, VCAM, IL-6, IL-8, B7-H4, serum amyloid A, transferrin, osteopontin, kallikreins, OVX1, VEGF, AGR-2, inhibin, M-CSF, uPAR, EGF receptor, lysophosphatidyl acid, beta2-microglobulin, miRNA, and Epstein-Barr virus (EBV) DNA. Exemplary biomarkers for prostate cancer include, without limitation, the prostate-specific antigen, FAM13C, KLK2, AZGP1, and SRD5A2. Exemplary biomarkers for lung cancer include, without limitation, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer.

Cancer biomarkers may be useful in determining the aggressiveness of an identified cancer as well as its likelihood of responding to the treatment. Examples of such prognostic biomarkers include, without limitation, CA125, beta2-microglobulin, and EBV DNA.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g. an ELISA).

As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the concentration of the biomarker is measured before and after the administration. When the concentration of the biomarker is maintained, the method may further comprise increasing the effective amount of the gold(III) complex(es) by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount.

In some embodiments, the mutation in the biomarker is detected before administering the composition to identify subjects predisposed to the disease. For example, subjects with a BRCA1 germline mutation are at a higher risk of contracting breast cancer, ovarian cancer, or prostate cancer.

In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

In some embodiments, the administering of the gold(III) complex(es) results in minimal therapy-induced toxicity and/or undesirable side effects. Examples of toxicity include, without limitation, peripheral neuropathy, nephrotoxicity, cardiotoxicity, pulmonary toxicity, blood toxicity, reproductive toxicity, dermal toxicity, hepatotoxicity, genotoxicity, and retinal toxicity. The toxicity may be apparent when the tissue is damaged and/or the gene(s) has mutations and may result in malfunctioning of the organ(s). In preferred embodiments, the toxicity is peripheral neuropathy and/or nephrotoxicity.

Symptoms of therapy-induced peripheral neuropathy include, without limitation, sensory impairment, sensorimotor neuropathy, pure motor neuropathy, distal axonopathy, paraesthesia, allodynia, and hyperalgesia. Peripheral neuropathy may be diagnosed and/or quantified with methods such as quantitative sensory testing (QST), nerve conduction tests, laser-Doppler-imager (LDI) flare, and biopsy. The subject with therapy-induced peripheral neuropathy may have: (1) a neuropathy disability score (on a scale of 0 to 10) of at least 4, at least 5, or at least 6, and up to 10; (2) a vibration perception threshold of at least 12 V, at least 15 V, or at least 18 V, and up to 20 V, 25 V, or 30V; and/or (3) a LDI flare area of not more than 3 cm$^2$, 4 cm$^2$, or 5 cm$^2$. The subject treated with the gold(II) complex(es) may have: (1) a neuropathy disability score (on a scale of 0 to 10) of not more than 1; (2) a vibration perception threshold of at least 5 V, at least 6 V, or at least 7 V, and up to 8 V, 9 V, or 10V; and/or (3) a LDI flare area of at least 5 cm$^2$, 6 cm$^2$, or 7 cm$^2$, and up to 8 cm$^2$, 9 cm$^2$, or 10 cm$^2$.

Symptoms of therapy-induced nephrotoxicity include, without limitation, excess urea in the blood (azotemia), anemia, increased hydrogen ion concentration in the blood (acidosis), excess fluids in the body (overhydration), and high blood pressure (hypertension). Cancer therapy-induced nephrotoxicity may be monitored by measuring the levels of the biomarkers such as serum creatinine (SCr), blood urea nitrogen (BUN), urinary kidney injury molecule-1 (KIM-1), neutrophil gelatinase-associated lipocalin (NGAL), interleukin-18 (IL-18), cystatin C, clusterin, fatty acid binding protein-liver type (L-FABP), nuclear factor kappa-light-chain-enhancer of activated B cells (NF-κB), and osteopontin. In a subject diagnosed with therapy-induced nephrotoxicity, the level of serum creatinine and/or blood urea nitrogen may be at least 10%, 20%, or 30% higher than the level of the respective biomarker in a subject administered with the gold(III) complex. A level of serum creatinine in a subject without cancer therapy-induced nephrotoxicity may be 0.4-1.3 mg/dL, 0.5-1.2 mg/dL, or 0.6-1.1 mg/dL. A level of blood urea nitrogen in a subject without cancer therapy-induced nephrotoxicity may be 5-20 mg/dL, 6-18 mg/dL, or 10-15 mg/dL. A subject without cancer therapy-induced nephrotoxicity may have a NF-κB level not more than 80%, 70%, 60%, 50%, 40%, or 30% of a NF-κB level in a subject experiencing cancer therapy-induced nephrotoxicity, or a NF-κB level not more than 1%, 2%, 3%, 4%, or 5% of a NF-κB level in a normal, healthy subject. The methods for determining the levels of the biomarkers are described above.

In some embodiments, the quantification of the neuropathy/nephrotoxicity biomarker and/or the diagnosis of neuropathy may be performed before and/or after the administration of the gold(III) complex(es). In some embodiments, the peripheral neuropathy/nephrotoxicity biomarkers are measured/detected after the administering of each dose of gold(III) complex(es). For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the ability of the active ingredient to reduce the viability of cancer cells may be determined by contacting a cytotoxic effective amount of the active ingredient with the cancer cells and then performing cell viability assays. Examples of such assays include, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. In a preferred embodiment, a MTT assay is used.

The cytotoxic effective amount of the active ingredient may be in a range of 0.01-100 μM, 0.1-80 μM, 1-60 μM, or 10-40 μM. As used herein, the term "cytotoxic effective amount" refers to a concentration of the active ingredient that reduces the viability of the cancer cells by at least 5%, 10%, 15%, 20%, 30%, 40%, 50%, 60%, 70%, 80% or 90%, relative to cancer cells not treated with the active ingredient. The reduction in viability may occur not more than 10 days, 7 days, 5 days, 3 days, or 2 days after the active ingredient is contact with the cancer cells. In one embodiment, the cytotoxic effective amount may be the $IC_{50}$ which is a concentration of the active ingredient which causes the death of 50% of cancer cells in 72 hours (3 days).

In some embodiments, the cytotoxic effective amount of the gold complex(es) may be 0.1-3, 0.5-2.5, or 1-2 orders of magnitude smaller than the cytotoxic effective amount of a platinum-based drug (e.g., cisplatin) (see Tables 2 and 3).

In at least one embodiment, the cancer cells are human cancer cells. The cancer cells may be derived from commercial cell lines, such as HeLa cervical cancer cells, non-small cell lung cancer cell lines (H460, A549, H226, H838, H157, H1975, H2122, SKLU1 and H1299), HCT15 colon cancer cells, HCT8 or HRT8 colon cancer cells, HCT116 colon cancer cells, DLD1 colon cancer cells, MCF7 breast cancer cells, MDA-MB231 breast cancer cells, A2780 ovarian cancer cells, HePG2 liver cancer cells, AsPC1 pancreatic cancer cells, PANC1 pancreatic cancer cells, PC3 androgen-resistant prostate cancer cells, DU 145 prostate cancer cells, and L540 Hodgkin lymphoma cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis ovarian cancer cells, A2780CP-16 ovarian cancer cells, and SGC7901-cis gastrointestinal cancer cells. In other embodiments, the human cancer cells are cancer cells of a human patient who has been diagnosed with at least one form of cancer, preferably breast cancer and/or pancreatic cancer.

In some embodiments, the active ingredient may be selective toward cancer cells and is non-toxic toward normal (i.e., non-cancerous) cells. In the context of the disclosure, the term "non-toxic" means that the active ingredient does not inhibit the proliferation of the normal cells when compared to normal cells treated with only DMSO. Exemplary normal cells include, without limitation, primary epidermal keratinocytes, primary gingival keratinocytes, primary bladder epithelial cells, primary bronchial/tracheal epithelial cells, and primary mammary epithelial cells. The primary cells may be obtained from the American Type Culture Collection (ATCC).

Having generally described this disclosure, a further understanding can be obtained by reference to certain specific examples which are provided herein for purposes of illustration only and are not intended to be limiting unless otherwise specified.

Example 1 Materials and Methods

Sodium tetrachloroaurate(III) dihydrate, sodium dimethyldithiocarbamate monohydrate, sodium diethyldithiocarbamate trihydrate, sodium dibenzyldithiocarbamate hydrate, 2,2'-bipyridine, 5,5'-dimethyl-2,2'-bipyridine and 6,6'-dimethyl-2,2'-bipyridine were purchased from Sigma-Aldrich Co. St. Louis, Mo. United States. All solvents including ethanol and dichloromethane were purchased from Merck Darmstadt, Germany, and used without further purification. All reactions were carried out under ambient conditions.

Elemental analyses of gold(III) compounds 1 to 9 were performed on Perkin Elmer Series 11 (CHNS/O) Analyzer 2400. The solid state FTIR spectra of free ligands and their corresponding gold(III) compounds were recorded on a Perkin-Elmer FTIR 180 spectrophotometer or NICOLET 6700 FTIR using potassium bromide (KBr) pellets over the range 4000-400 $cm^{-1}$.

$^1H$ and $^{13}C$ NMR spectra were recorded on a LAMBDA 500 spectrophotometer operating at 500.01, 125.65 and 200.0 MHz, respectively, in a magnetic field of 11.74 T. The nucleus observed at 500 MHz. Tetramethylsilane (TMS) was used as an internal standard for $^1H$ and $^{13}C$. The $^{13}C$ NMR spectra were obtained with $^1H$ broadband decoupling, and the spectral conditions were: 32 k data points, 0.967 s acquisition time, 1.00 s pulse delay, and 45° pulse angle.

Example 2 Synthesis of Complexes

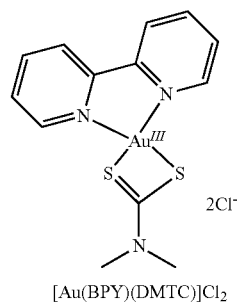

(1)

[Au(BPY)(DMTC)]Cl$_2$

Compound 1 was synthesized in a stepwise manner. Na[AuCl$_4$].2H$_2$O, 0.5 mM (200 mg) and 2,2'-bipyridine 0.5 mM (78 mg) were added simultaneously to 20 mL of ethanol and the mixture was stirred for 3 h at room temperature. The sodium dimethyldithiocarbamate dihydrate 0.5 mM (72 mg) in 10 mL distilled water was added slowly in the pale yellow turbid solution obtained from the previous step. The reaction mixture was stirred for an additional 1 h at room temperature. The final product appeared as light yellow precipitate in solution. The precipitate was collected by filtration, washed with fresh distilled water (3×10 mL) and dried at room temperature under vacuum. Yield: 83.09% (219.98 mg). FT-IR (KBr, $v_{max}$, $cm^{-1}$): 3570 (m), 3045 (w), 2926 (w); 1586 (m), 1482 (s), 1242 (m), 1159 (w), 1039 (m), 993 (m), 967 (w), 761 (s), 565 (m), 439 (m). $^1H$ NMR (500 MHz, DMSO-d$_6$): δ=3.36 (6H, 2×CH), 7.55, 8.06, 8.44 and 8.73 (2H, 2×CH, BPY), $^{13}C$ NMR (125.1 MHz, DMSO-d$_6$): δ=40.29 (CH$_3$), 121.65, 125.19, 139.20 and 148.50 (2,2'-BPY), 189.87 (NC=S). Anal. calc. for C$_{13}$H$_{14}$Cl$_2$N$_3$S$_2$Au (544.27): C, 28.69; H, 2.59; N, 7.72; S, 11.78%. Found: C, 28.55; H, 2.51; N, 7.75; S, 11.80%.

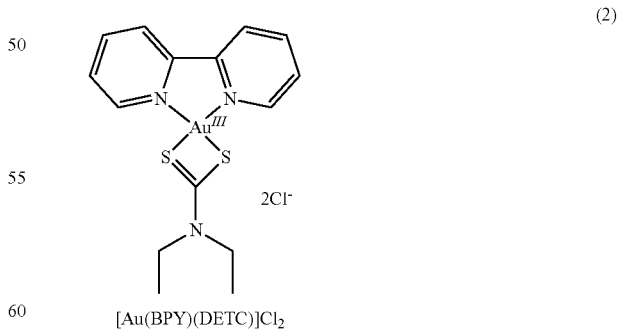

(2)

[Au(BPY)(DETC)]Cl$_2$

Compound 2 was synthesized according to the procedure as mention above for compound 1. The solution of sodium diethyldithiocarbamate trihydrate 1.0 mM (226 mg) in 10 mL of distilled water was added slowly to the reaction mixture obtained from the first step as described above for compound 1 and was stirred for 1 h at room temperature. The final product of compound 2 appeared as yellow precipitate in the reaction medium. The product was collected by filtration, washed with fresh distilled water (3×10 mL) and dried at room temperature under vacuum for 24 h. The product appeared as yellow crystalline powder. Yield: 86.87% (166.87 mg). FT-IR (KBr, $v_{max}$, cm$^{-1}$): 3568 (m), 3048 (w), 2923 (w); 1583 (m), 1485 (s), 1247 (m), 1155 (w), 1038 (m), 988 (m), 958 (w), 768 (s), 555 (m), 435 (m). $^1$H NMR (500 MHz, DMSO-d$_6$): δ=1.25 (6H, 2×CH$_3$), 3.76 (4H, 2×CH$_2$), 7.60, 8.11, 8.49 and 8.76 (2H, 2×CH, BPY), $^{13}$C NMR (125.1 MHz, DMSO-d$_6$): δ=12.07 (CH$_3$), 46.57 (CH$_2$), 121.63, 125.23, 139.23 and 148.36 (2,2'-BPY), 193.88 (NC=S). Anal. calc. for C$_{15}$H$_{18}$Cl$_2$N$_3$S$_2$Au (572.33): C, 31.48; H, 3.17; N, 7.34; S, 11.21%. Found: C, 31.37; H, 3.08; N, 7.19; S, 11.15%.

(3)

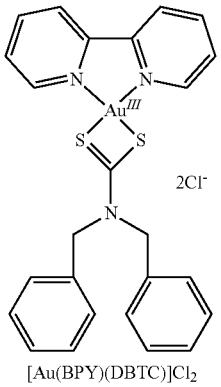

[Au(BPY)(DBTC)]Cl$_2$

Compound 3 was synthesized according to the procedure as mention above for compounds 1 and 2. The solution of sodium dibenzyldithiocarbamate hydrate 0.5 mM (148 mg) in 10 mL distilled water was added slowly in the reaction mixture of Na[AuCl$_4$].2H$_2$O, 0.5 mM (200 mg) and 2,2'-bipyridine 0.5 mM (78 mg) as described above for compound 1 and stirred at room temperature for 1 h. The final product appeared as brown lumps in solution. The solid product was collected by filtration, washed with fresh distilled water (3×10 mL) and dried at room temperature under vacuum for 24 h. Yield: 85.55% (226.13 mg). FT-IR (KBr, $v_{max}$, cm$^{-1}$): 3587 (m), 3143 (w), 2925 (w); 1552 (s), 1481 (m), 1224 (m), 1120 (w), 1078 (m), 981 (m), 916 (w), 551 (m), 473 (m). $^1$H NMR (500 MHz, DMSO-d$_6$): δ=5.03 (4H, 2×CH$_2$), 7.38 (10H, 2×C$_6$H$_5$), 7.47, 7.96, 8.39 and 8.69 (2H, 2×CH, BPY), $^{13}$C NMR (125.1 MHz, DMSO-d$_6$): δ=55.18 (CH$_2$), 120.67, 124.43, 137.73 and 149.08 (2,2'-BPY), 128.24-132.50 and 154.64 (C$_6$H$_5$), 191.76 (NC=S). Anal. calc. for C$_{25}$H$_{22}$Cl$_2$N$_3$S$_2$Au (696.46): C, 43.11; H, 3.18; N, 6.03; S, 9.21%. Found: C, 43.33; H, 3.15; N, 6.20; S, 9.33%.

(4)

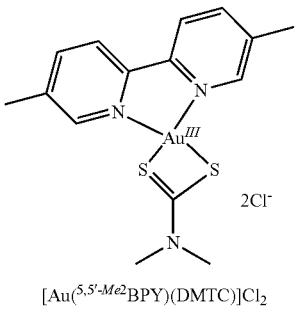

[Au($^{5,5'-Me2}$BPY)(DMTC)]Cl$_2$

The compound 4 was synthesized by following the same procedure as described for compound 1 with minor modifications. Na[AuCl$_4$].2H$_2$O, 0.5 mM (200 mg) and 5,5'-dimethyl-2,2'-dipyridyl 0.5 mM (92 mg) were added simultaneously in 20 mL of ethanol and the mixture was stirred for 3 h at room temperature. Sodium dimethyldithiocarbamate dihydrate 0.5 mM (72 mg) in 10 mL distilled water was added slowly to the bright yellow turbid solution formed in the preceding step. The reaction mixture was stirred for 1 h at room temperature. The final product appeared as pale yellow precipitates in solution. The precipitates were collected by filtration, washed with fresh distilled water (3×10 mL) and dried at room temperature under vacuum. Yield: 80.09% (187.27 mg). FT-IR (KBr, $v_{max}$, cm$^{-1}$): 3373 (m), 3037 (w), 2922 (w), 1555 (s), 1477 (s), 1272 (m), 1155 (m), 1028 (m), 981 (m), 896 (w), 567 (s), 468 (m). $^1$H NMR (500 MHz, DMSO-d$_6$): δ=2.37 (6H, 2×CH), 3.35 (6H, 2×CH$_3$), 7.85, 8.31 and 8.53 (2H, 2×CH, BPY), $^{13}$C NMR (125.1 MHz, DMSO-d$_6$): δ=17.78 (CH$_3$), 40.29 (CH$_3$), 121.28, 135.33, 140.27 and 147.80 (2,2'-BPY), 193.87 (NC=S). Anal. calc. for C$_{15}$H$_{18}$Cl$_2$N$_3$S$_2$Au (572.33): C, 31.48; H, 3.17; N, 7.34; S, 11.21%. Found: C, 31.50; H, 3.08; N, 7.25; S, 11.17%.

(5)

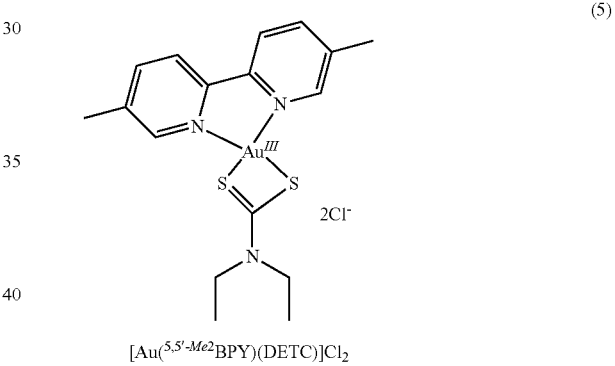

[Au($^{5,5'-Me2}$BPY)(DETC)]Cl$_2$

Compound 5 was synthesized according to the procedure as mentioned above for compound 4. The solution of sodium diethyldithiocarbamate trihydrate 1.0 mM (226 mg) in 10 mL of distilled water was added slowly to the reaction mixture of first step as described above for compound 4 and was stirred for 1 h at room temperature. The final product appeared as deep yellow precipitate in the reaction medium. The product was collected by filtration, washed with fresh distilled water (3×10 mL) and dried at room temperature under vacuum for 24 b. The product appeared as yellow crystalline powder. Yield: 88.51% (343.9 g). FT-IR (KBr, $v_{max}$, cm$^{-1}$): 3384 (w), 3035 (w), 2983 (w), 2926 (w), 1572 (s), 1473 (s), 1350 (m), 1220 (s), 1130 (m), 1056 (m), 996 (m), 827 (m), 538 (s), 465 (m). $^1$H NMR (500 MHz, DMSO-d$_6$): δ=1.27 (6H, 2×CH$_3$), 2.37 (6H, 2×CH$_3$), 3.76 (4H, 2×CH$_2$), 7.85, 8.31 and 8.53 (2H, 2×CH, BPY), $^{13}$C NMR (125.1 MHz, DMSO-d$_6$): δ=12.05 (CH$_3$), 17.80 (CH$_3$), 46.55 (CH$_2$), 120.41, 134.23, 138.83 and 148.64 (2,2'-BPY), 193.89 (NC=S). Anal. calc. for C$_{17}$H$_{22}$Cl$_2$N$_3$S$_2$Au (600.38): C, 34.01; H, 3.69; N, 7.00; S, 10.68%. Found: C, 33.91; H, 3.64; N, 7.18; S, 10.59%.

(6)

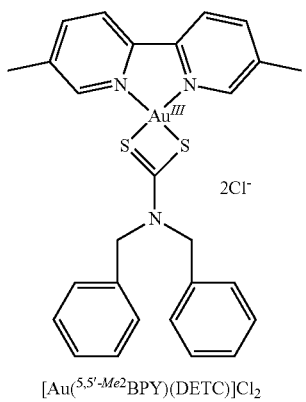

[Au(5,5'-Me2BPY)(DETC)]Cl2

Compound 6 was synthesized according to the procedure as mentioned above for compound 4. The solution of sodium dibenzyldithiocarbamate hydrate 0.5 mM (148 mg) in 10 mL of distilled water was added slowly to the reaction mixture of first step as described above for compound 4 and was stirred for 1 h at room temperature. The final product appeared as yellowish green precipitates in solution. The product was collected by filtration, washed with fresh distilled water (3×10 mL) and dried at room temperature under vacuum for 24 b. Yield: 78.01% (256.6 mg). FT-IR (KBr, $v_{max}$, cm$^{-1}$): 3388 (w), 3031 (w), 2993 (w), 2923 (m), 1553 (s), 1470 (s), 1345 (m), 1224 (s), 1123 (m), 1077 (m), 980 (s), 828 (m), 553 (s), 466 (m). $^1$H NMR (500 MHz, DMSO-d$_6$): δ=2.38 (6H, 2×CH$_3$), 5.02 (4H, 2×CH$_2$), 7.37 (10H, 2×C$_4$H$_5$), 7.90, 8.33 and 8.57 (2H, 2×CH, BPY), $^{13}$C NMR (125.1 MHz, DMSO-d$_6$): δ=17.77 (CH$_3$), 55.38 (CH$_2$), 120.78, 134.69, 139.43 and 148.29 (2,2'-BPY), 128.25-132.52 and 150.13 (C$_6$H$_5$), 191.77 (NC=S). Anal. calc. for C$_{27}$H$_{26}$Cl$_2$N$_3$S$_2$Au (724.52): C, 44.76; H, 3.62; N, 5.80; S, 8.85%. Found: C, 44.73; H, 3.70; N, 5.77; S, 8.90%.

(7)

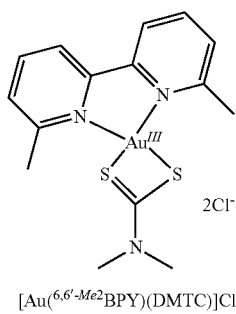

[Au(6,6'-Me2BPY)(DMTC)]Cl2

Compound 7 was synthesized by following the same procedure as described for compound 1 with minor modifications. Na[AuCl$_4$]H$_2$O, 0.5 mM (200 mg) and 6,6'-dimethyl-2,2'-dipyridyl 0.5 mM (92 mg) were added simultaneously in 20 mL of ethanol and mixture was stirred for 3 h at room temperature. The sodium dimethyldithiocarbamate dihydrate 0.5 mM (72 mg) in 10 mL distilled water was added slowly in the bright yellow solution of above reaction mixture. The reaction mixture was stirred for 1 h at room temperature. The final product appeared as light yellow precipitates in solution. The precipitates were collected by filtration, washed with fresh distilled water (3×10 mL) and dried at room temperature under vacuum. Yield: 90.09% (187.27 mg). FT-IR (KBr, $v_{max}$, cm$^{-1}$): 3378 (m), 3033 (w), 2925 (w), 1575 (s), 1477 (s), 1238 (m), 1162 (m), 1046 (m), 998 (m), 868 (w), 567 (s), 440 (m). $^1$H NMR (500 MHz, DMSO-d$_6$): δ=2.49 (6H, 2×CH$_3$), 3.36 (6H, 2×CH$_3$), 7.41, 7.93 and 8.22 (2H, 2×CH, BPY), $^{13}$C NMR (125.1 MHz, DMSO-d$_6$): δ=13.77 (CH$_3$), 45.25 (CH$_3$), 119.15, 125.21, 139.47 and 158.57 (2,2'-BPY), 187.83 (NC=S). Anal. calc. for C$_{15}$H$_{18}$Cl$_2$N$_3$S$_2$Au (572.33): C, 31.48; H, 3.17; N, 7.34; S, 11.21%. Found: C, 31.67; H, 3.29; N, 7.38; S, 11.09%.

(8)

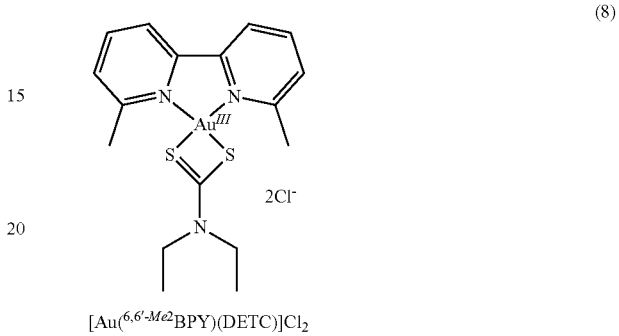

[Au(6,6'-Me2BPY)(DETC)]Cl2

Compound 8 was synthesized according to the procedure as mentioned above for compound 7. The solution of sodium diethyldithiocarbamate trihydrate 1.0 mM (226 mg) in 10 mL of distilled water was added slowly to the reaction mixture of first step as described above for compound 4 and was stirred for 1 h at room temperature. The final product appeared as yellow precipitates in the reaction medium. The product was collected by filtration, washed with fresh distilled water (3×10 mL) and dried at room temperature under vacuum for 24 h. Yield: 68.51% (343.9 g). FT-IR (KBr, $v_{max}$, cm$^{-1}$): 3418 (w), 3029 (w), 2978 (w), 2925 (w), 1574 (s), 1479 (s), 1351 (m), 1281 (s), 1154 (m), 1081 (m), 988 (m), 847 (m), 585 (s), 415 (m). $^1$H NMR (500 MHz, DMSO-d$_6$): δ=1.27 (6H, 2×CH$_3$), 2.49 (6H, 2×CH$_3$), 3.76 (4H 2×CH$_2$), 7.42, 7.92 and 8.23 (2H, 2×CH, BPY), $^{13}$C NMR (125.1 MHz, DMSO-d$_6$): δ=13.07 (CH$_3$), 24.96 (CH$_3$), 47.71 (CH$_2$), 119.50, 125.28, 139.52 and 158.55 (2,2'-BPY), 188.12 (NC=S). Anal. calc. for C$_{17}$H$_{22}$Cl$_2$N$_3$S$_2$Au (600.38): C, 34.01; H, 3.69; N, 7.00; S, 10.68%. Found: C, 34.25; H, 3.51; N, 7.29; S, 10.48%.

(9)

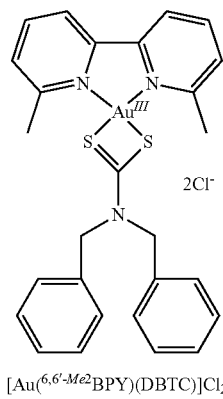

[Au(6,6'-Me2BPY)(DBTC)]Cl2

Compound 9 was synthesized according to the procedure as mentioned above for compound 7. The solution of sodium dibenzyldithiocarbamate hydrate 0.5 mM (148 mg) in 10 mL of distilled water was added slowly to the reaction mixture of first step as described above for compound 7 and was stirred for 1 h at room temperature. The final product appeared as reddish brown precipitates in solution. The product was collected by filtration, washed with fresh distilled water (3×10 mL) and dried at room temperature under vacuum for 24 h. Yield: 65.01% (256.6 mg). FT-IR (KBr, $v_{max}$, cm$^{-1}$): 3428 (w), 3035 (w), 2978 (w), 2922 (m), 1566 (s), 1475 (s), 1331 (m), 1251 (s), 1119 (m), 1082 (m), 985 (s), 808 (m), 515 (s), 436 (m). $^1$H NMR (500 MHz, DMSO-d$_6$): δ=2.48 (6H, 2×CH$_3$), 5.01 (4H, 2×CH$_2$), 7.36 (10H, 2×C$_6$H$_5$), 7.41, 7.91 and 8.20 (2H, 2×CH, BPY), $^{13}$C NMR (125.1 MHz, DMSO-d$_6$): δ=24.92 (CH$_3$), 54.88 (CH$_2$), 118.95, 125.18, 138.33 and 157.43 (2,2'-BPY), 128.27-131.52 and 151.11 (C$_6$H$_5$), 199.01 (NC=S). Anal. calc. for C$_{27}$H$_{26}$Cl$_2$N$_3$S$_2$Au (724.52): C, 44.76; H, 3.62; N, 5.80; S, 8.85%. Found: C, 44.33; H, 3.490; N, 5.63; S, 8.75%.

Characterization of Gold(III) Complexes by FT-IR

Gold(III) mixed-ligand compounds 1 to 9 were identified by the presence of the stretching bands around 3030 and 2925 cm$^{-1}$ assigned to C—H stretch in the: (1) aromatic (phenyl and 2,2'-dipyridyl) and (2) saturated aliphatic methyl and ethyl groups of coordinated ligands, respectively. All gold(III) compounds exhibited characteristic absorbance peaks for v(C—N) and v(C—S). The infrared region 1480-1550 cm$^{-1}$ was assigned to the R$_2$N—CSS 'thioureide' band in the IR spectra of dithiocarbamate compounds. This band indicated the carbon-nitrogen bond order may be between a single bond at 1250-1350 cm$^{-1}$ and a double bond at 1640-1690 cm$^{-1}$ (Odola, A. J.; Woods, J. A. O. New nickel (II) mixed ligand complexes of dithiocarbamates with Schiff base. *Chem. Pharm. Res.* 2011, 3, 865-871, incorporated herein by reference in its entirety). The thioureide band, v(C—N) was detected at 1470-1490 cm$^{-1}$ in compounds 1 to 9. These frequency absorption bands were between those associated with single C—N and double C=N bonds. Hence, the partial double bond character of 'thioureide' bond was confirmed for all gold(II) compounds (Altaf, M.; Isab, A. A.; Vančo, J.; Dvořák, Z.; Trhvníček, Z.; Stoeckli-Evans, H. Synthesis, characterization and in vitro cytotoxicity of gold(III) dialkyl/diaryldithiocarbamato complexes. *RSC Advances.* 2015, 5, 81599-81607, incorporated herein by reference in its entirety). The presence of a strong absorption band in the range of 1470-1550 cm$^{-1}$ in FTIR spectra clearly indicated the formation of dithiocarbamato gold(III) compounds (Jayaraju, A.; Ahamad, M. M.; Rao, R. M.; Sreeramulu, J. Synthesis, characterization and biological evaluation of novel dithiocarbamate metal complexes. *Der. Pharma. Chemica.* 2012, 4, 119-194; and Altaf, M.; Monin-ul-Mehboob, M.; Seliman, A. A. A.; Isab. A. A.; Dhuna, V.; Bhatia, G.; Dhuna, K. Synthesis, characterization and anticancer activity of gold (1) complexes that contain tri-tert-butylphosphine and dialkyl dithiocarbamate ligands. *J. Organomet. Chem.* 2014, 765, 68-79, each incorporated herein by reference in their entirety). Similarly, a C=S stretch band with a medium intensity around 1070 and 970 cm$^{-1}$ for compounds 1 to 9 was an additional evidence of the formation of mixed ligands compounds. These absorption bands were comparable to the free sodium salt of diethyldithiocarbamate ligands (Pouchert, C. J. Aldrich Library of FT-IR Spectra, 2nd ed., Aldrich Chemical Company, Milwaukee, 1997, incorporated herein by reference in its entirety).

Characterization by NMR

A slight downfield and upfield shifts for protons of the coordinated dimethyl dithiocarbamate, diethyl dithiocarbamate, and dibenzyldithiocarbamate in gold(III) compounds 1 to 9 were observed when compared to free dialkyl/diaryldithiocarbamate ligands (Che, C.-M.; Sun, R. W.-Y. Therapeutic applications of gold complexes: lipophilic gold(III) cations and gold (I) complexes for anticancer treatment. *Chem. Commun.*, 2011, 47, 9554-9560; Calami, P.; Carotti, A.; Guerri, T.; Messori, L.; Mini, E.; Orioli, P.; Speroni, G. P. Biological properties of two gold(III) complexes: AuCl$_3$(Hpm) and AuCl$_2$(pm). *J. Inorg. Biochem.* 1997, 66, 103-109C Johnson, R. K.; Mirabelli, C. K.; Faucette, L. F.; McCabe, F. L.; Sutton, B. M.; Bryan, D. L.; Girard, G. R.; Hill, D. T. Antitumor-activity of compounds related to bis(diphenylphosphine)ethane and its chlorogold (I) coordination. *Proc. Amer. Assoc. Cancer Res.* 1985, 26, 254-8; Mirabelli, C. K.; Faucette, L. F.; McCabe, F. L.; Sutton, B. M.; Bryan. D. L.; Girard, G. R.; Hill, D. T.; Bartus, J. O.; Crooke, S. T.; Johnson, R. K. Antitumor activity of bis (diphenylphosphino) alkanes, their gold (1) coordination complexes, and related compounds. *J. Med. Chem.* 1987, 30, 2181-2190; Ronconi, L.; Giovagnini, L.; Marzano, C.; Bettio, F.; Graziani, R.; Pilloni, G.; Fregona, D. Gold dithiocarbamate derivatives as potential antineoplastic agents: design, spectroscopic properties, and in vitro antitumor activity. *Inorg. Chem.* 2005, 44, 1867-1881; Altaf, M.; Monim-ul-Mehboob, M.; Seliman, A. A. A.; Sohail, M.; Wazeer, M. I. M.; Isab, A. A.; Li, L.; Dhuna, V.; Bhatia, G.; Dhuna, K. Synthesis, characterization and anticancer activity of gold (II) complexes that contain tri-tert-butylphosphine and dialkyl dithiocarbamate ligands. *Eur. J. Med. Chem.* 2015, 95, 464-472; and Altaf. M., Monim-ul-Mehboob, M.; Isab, A. A.; Dhuna, V.; Bhatia, G.; Dhuna, K.; Altuwaijri, S. The synthesis, spectroscopic characterization and anticancer activity of new mono and binuclear phosphanegold (I) dithiocarbamate complexes. *New J. Chem.* 2015, 39, 377-385, each incorporated herein by reference in their entirety).

The $^{13}$C NMR spectra of compounds 4 and 7 showed seven resonances, and the $^{13}$C NMR spectra of compound 1 showed six resonances. This data confirmed the coordination of dimethyldithiocarbamato and bipyridyl ligands with the gold(III) ion. The $^{13}$C NMR spectra of compounds 5, 8, and 2 showed one additional resonance when compared to the spectra of compounds 4, 7, and 1, respectively. Multiple resonances were observed in the $^{13}$C NMR spectra of compounds 3, 6, and 9 due to the presence of dibenzyl and pyridyl functional groups. There was an upfield chemical shift of the NC=S carbon of the coordinated dialkyl/diaryldithiocarbamate ligands with respect to free dialkyl/diaryldithiocarbamate ligands for all gold(III) compounds. The $^{13}$C chemical shifts of the NC=S carbon in the bonded dimethyldithiocarbamate, diethyldithiocarbamate, and dibenzyldithiocarbamate were observed in the range of 186-200 ppm for our synthesized compounds 1 to 9.

Example 3 Cell Lines and Culture Conditions

Hodgkin's lymphoma cell line (L-540) and human androgen-resistant prostate cancer cell line (PC3) were obtained from the German Collection of Microorganisms and Cell Cultures (Braunschweig, Germany). Human breast adenocarcinoma cell line MCF-7 cell line (HTB-22™) was obtained from the American Type Culture Collection (ATCC, Rockville, Md., USA). Human ovarian epithelial carcinoma-derived cancer cells A2780 and its cisplatin-resistant clone A2780cis were from Sigma Inc (St. Louis, Mo., USA), and the isogenic cisplatin-resistant 2780CP-16 cells were cultured as previously described (Siddik, Z. H.;

Mims, B.; Lozano, G.; Thai, G. Independent pathways of p53 induction by cisplatin and X-rays in a cisplatin-resistant ovarian tumor cell line. *Cancer Res.* 1998, 58, 698-703, incorporated herein by reference in its entirety). A panel of non-small cell lung cancer (NSCLC) cell lines (H460, A549, H226, H838, H157, H1975, H2122, SKLU1 and H1299) was obtained from Dr. Garth Powis at MD Anderson Cancer Center. Cell lines were further authenticated for their origin by BMR Genomics according to Cell ID System (Promega) protocol and using Genemapper ID Ver 3.2.1 to identify DNA short tandem repeat profiles. The parent cisplatin-resistant subclone (A2780cis) was maintained by weekly treatment with 1 µM cisplatin (Casagrande, N.; Celegato, M.; Borghese, C.; Mongiat, M.; Colombatti, A.; Aldinucci, D. Preclinical activity of the liposomal cisplatin Lipoplatin in ovarian cancer. *Clin. Cancer Res.* 2014, 20(21), 5496-5506, incorporated herein by reference in its entirety). However, the resistance in 2780CP-16 cells was stable and did not require cisplatin maintenance.

Cells were cultured in 5% $CO_2$ in RPMI (for L-540, A2780, A2780cis, 2780CP-16, PC3 and the panel of lung cancer cells) or DMEM (for MCF-7 cells) media supplemented with 10% heat-inactivated fetal calf serum (FCS; Sigma-Aldrich-Italy), 0.2 mg/ml penicillin/streptomycin and 0.1% (w/v) L-gluamine (Biocrom) at 37° C. in a 5% $CO_2$ fully humidified atmosphere.

Example 4 Cell Proliferation Assay and p53 Knockdown

Gold(III) compounds were dissolved in DMSO (final concentration of the gold(III) complexes was 10 mM) and stored at −80° C. in volumes of 500 µL or aliquoted into volumes of 10 µL and stored at −20° C. (used once without refreezing). They were then diluted in RPMI medium immediately before use. The culture medium with the same amount of drug-free DMSO was used as negative control.

PC3 and MCF-7 cells ($2.5 \times 10^3$), A2780, A2780cis ($4.0 \times 10^3$), A2780CP-16 and lung cancer cells (H460, A549, H226, H838, H157, H1975, H2122, SKLU1 and H1299) were seeded in 96-well flat-bottomed microplates (100 µL) and incubated for 24 h (to allow cell adhesion) before drug testing. The medium was then removed and replaced with fresh medium which separately contained cisplatin and the gold(III) compounds 1 to 9 at increasing concentrations (from 0.01 to 100 µM) at 37° C. for 72-120 h. Each treatment was performed in triplicate. Cell proliferation was assayed using the MTT assay or the MTS assay. Alternatively, L-540 cells ($2.0 \times 10^5$/ml) were seeded in 96-well plates and treated as previously described (Celegato, M.; Borghese, C.; Casagrande. N.; Mongiat, M.; Kahle, X. U.; Paulitti, A.; Spina, M.; Colombatti, A.; Aldinucci, D. Preclinical activity of the repurposed drug Auranofin in classical Hodgkin lymphoma. *Blood.* 2015, 126(11), 1394-7, incorporated herein by reference in its entirety). After treatment, cell proliferation was evaluated by the MTS assay (Promega). $IC_{50}$ (i.e., the half maximal inhibitory concentration representing the concentration of a substance required for 50% in vitro inhibition of cell growth), $IC_{75}$ (i.e., the inhibitory concentration representing the concentration of a substance required for 75% in vitro inhibition of cell growth), and $IC_{90}$ (i.e., the inhibitory concentration representing the concentration of a substance required for 90% in vitro inhibition of cell growth) values were calculated using the CalcuSyn software (Biosoft, Ferguson, Mo., USA) and reported in Table 1 (Chou, T. C.; Talalay, P. Quantitative analysis of dose-effect relationships: the combined effects of multiple drugs or enzyme inhibitors. *Adv. Enzyme Regul.* 1984, 22, 27-55, incorporated herein by reference in its entirety). The dependency of the anticancer activity of the gold(III) compounds on the type of p53 or the absence of p53 was assessed in A2780 cells following p53 knockdown by CRISPR (Cong, L.; Ran, F. A.; Cox, D.; Lin, S.; Barretto, R.; Habib, N.; Hsu, P. D.; Wu, X.; Jiang, W.; Marraffini, L. A.; Zhang, F. Multiplex genome engineering using CRISPR/Cas systems Science. 2013, 15; 339 (6121), 819-23, incorporate herein by reference in its entirety). The $IC_{50}$, $IC_{75}$, and $IC_{90}$ values reported herein may be represented as the mean±SEM of three independent experiments.

TABLE 1

Growth inhibition by gold(III) compound 1 in A2780, A2780cis, MCF-7, PC3 and L-540 cells.

| | Compound 1 | | | | |
|---|---|---|---|---|---|
| | A2780 | A2780cis | MCF-7 | PC3 | L-540 |
| $IC_{50}$ (µM) | 0.18 ± 0.02 | 0.17 ± 0.01 | 0.27 ± 0.02 | 0.42 ± 0.04 | 2.68 ± 0.24 |
| $IC_{75}$ (µM) | 0.45 ± 0.04 | 0.43 ± 0.04 | 0.51 ± 0.05 | 0.73 ± 0.07 | 3.50 ± 0.32 |
| $IC_{90}$ (µM) | 0.60 ± 0.05 | 0.56 ± 0.06 | 0.74 ± 0.08 | 0.91 ± 0.11 | 4.20 ± 0.39 |

Gold(III) compounds (compounds 1 to 9) were tested for in vitro cytotoxicity toward human Hodgkin lymphoma (L-540), androgen-resistant prostate cancer (PC3), breast cancer (MCF-7), and ovarian adenocarcinoma cisplatin-sensitive (A2780) and cisplatin-resistant (A2780cis) cell lines. For comparison purposes, cisplatin activity was also evaluated.

In L-540 cells, gold(III) compounds showed an $IC_{50}$ higher or similar to that of cisplatin (Table 2). Compounds 3, 6, and 9 were less active than cisplatin in all cell lines tested showing higher or similar $IC_{50}$ values (Table 2 and 3). Their different cytotoxic activity may be due to the difference in chemical structures.

The other gold(III) compounds (1, 2, 4, 5, 7, and 8) were generally more effective than cisplatin and these gold(III) compounds had an $IC_{50}$ ranging from 0.27 to 0.47 µM in MCF-7 cells, from 0.42 to 1.6 µM in PC3 cells (see Table 2), from 0.18 to 0.73 µM in A2780 cells (see Table 3) and from 0.17 to 0.45 µM in its cisplatin-resistant clone A2780cis (see Table 3). Compound 1 showed the lowest $IC_{50}$ value in all the investigated tumor cell lines (see Tables 2 and 3) and its representative dose-response curves are shown in FIG. 1A (the results represent the mean±SEM of three independent experiments). Compound 1 induced apoptosis in A2780, A2780cis, MCF-7, PC3, and L-540. Further, compound 1 was about 60-fold to 80-fold more active than cisplatin in inhibiting cell proliferation of cisplatin-resistant ovarian adenocarcinoma A2780cis cells and breast cancer MCF-7 cells (see Tables 2 and 3).

TABLE 2

Growth inhibion by gold(III) compounds in MCF-7, PC3 and L-540 cells.

| | IC$_{50}$ (µM) | | |
|---|---|---|---|
| | MCF-7 | PC3 | L-540 |
| Cisplatin | 22.2 ± 0.20 | 3.30 ± 0.30 | 2.50 ± 0.10 |
| 1 | 0.27 ± 0.02 | 0.42 ± 0.04 | 2.68 ± 0.24 |
| 2 | 0.27 ± 0.02 | 0.70 ± 0.06 | 2.80 ± 0.25 |
| 3 | 23.0 ± 2.07 | 11.2 ± 1.00 | 12.0 ± 1.08 |
| 4 | 0.28 ± 0.02 | 0.59 ± 0.05 | 2.70 ± 0.22 |
| 5 | 0.29 ± 0.03 | 0.86 ± 0.08 | 2.90 ± 0.26 |
| 6 | 18.0 ± 1.62 | 11.6 ± 1.04 | 6.50 ± 0.06 |
| 7 | 0.35 ± 0.03 | 0.77 ± 0.07 | 3.60 ± 0.32 |
| 8 | 0.47 ± 0.04 | 1.60 ± 0.14 | 6.20 ± 0.56 |
| 9 | 31.0 ± 2.79 | 11.5 ± 1.03 | 35.75 ± 3.22 |

TABLE 3

Growth inhibition by gold(III) compounds in ovarian cancer cell lines A2780 and cisplatin-resistant A2780cis.

| | IC$_{50}$ (µM) | | Fold resistance A2780cis/A2780 |
|---|---|---|---|
| Compound | A2780 | A2780cis | ratio |
| Cisplatin | 1.5 ± 0.1 | 10.4 ± 0.9 | 6.93 |
| 1 | 0.18 ± 0.02 | 0.17 ± 0.01 | 0.94 |
| 2 | 0.24 ± 0.02 | 0.18 ± 0.01 | 0.58 |
| 3 | 4.66 ± 0.13 | 14.3 ± 1.12 | 3.07 |
| 4 | 0.28 ± 0.03 | 0.17 ± 0.01 | 0.94 |
| 5 | 0.59 ± 0.05 | 0.23 ± 0.02 | 0.39 |
| 6 | 6.35 ± 0.06 | 15.7 ± 1.41 | 2.47 |
| 7 | 0.27 ± 0.02 | 0.23 ± 0.02 | 0.85 |
| 8 | 0.73 ± 0.06 | 0.45 ± 0.03 | 0.62 |
| 9 | 6.7 ± 0.6 | 16.0 ± 1.44 | 2.39 |

As the response to chemotherapy can be influenced by the status of the tumor suppressor TP53 gene, four p53 wild-type (WT-p53), four p53 mutant (Mut-p53) and one p53 deleted (Null-p53) were utilized to determine whether the gold compounds have p53 dependence.

Figure 3A:
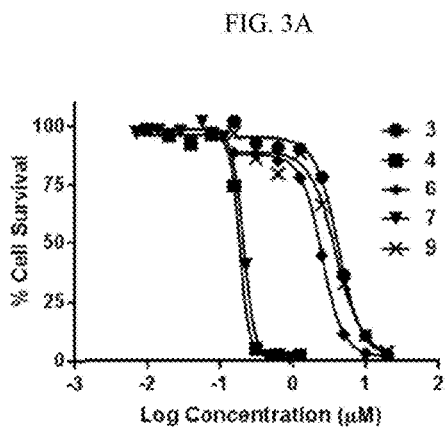
FIG. 3A shows the sigmoidal dose-response curves for A549 cells obtained 5 days after contacting the cells with compounds 3, 4, 6, 7, and 9.
Figure 3B:
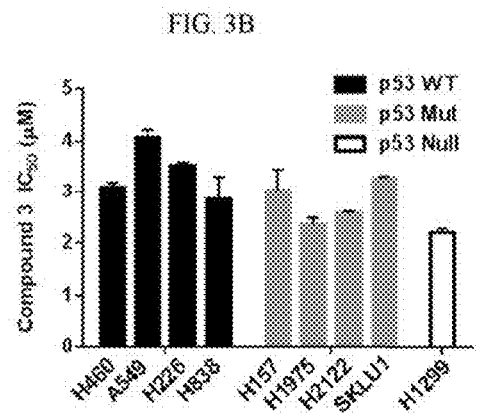
FIG. 3B shows the $IC_{50}$ values of compound 3 for NSCLC cells grouped by p53 status.
Figure 3C:
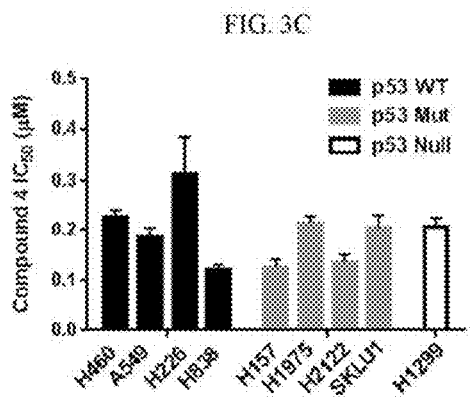
FIG. 3C shows the $IC_{50}$ values of compound 4 for NSCLC cells grouped by p53 status.
Figure 3D:
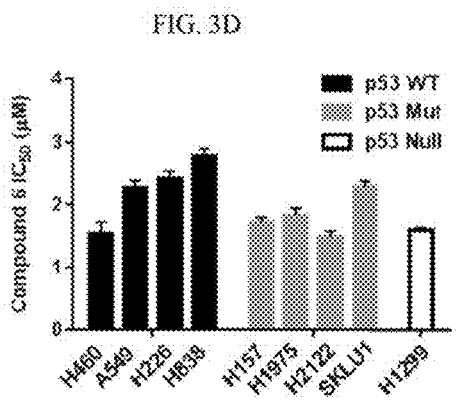
FIG. 3D shows the $IC_{50}$ values of compound 6 for NSCLC cells grouped by p53 status.
Figure 3E:
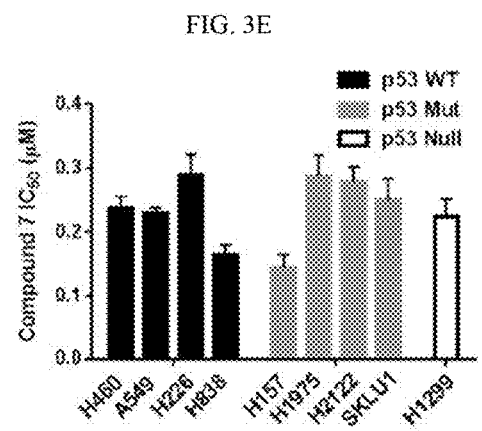
FIG. 3E shows the $IC_{50}$ values of compound 7 for NSCLC cells grouped by p53 status.
Figure 3F:
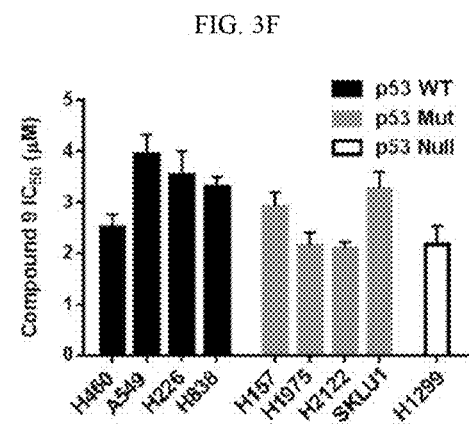
FIG. 3F shows the $IC_{50}$ values of compound 9 for NSCLC cells grouped by p53 status.
Figure 4:
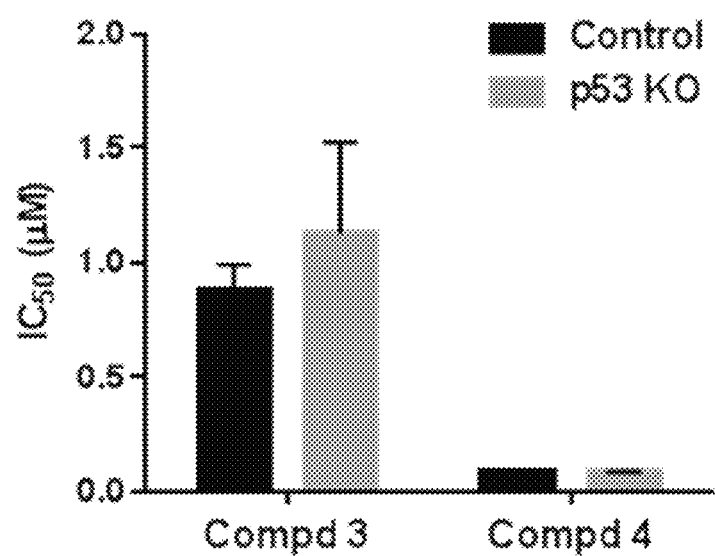
FIG. 4 shows the $IC_{50}$ values for compounds 3 and 4 in an A2780 clone following transfection with either CRISPR control (Control) or CRISPR p53-sgRNA plasmid (p53 KO).

Compounds 3, 4, 6, 7, and 9 showed an IC$_{50}$ ranging between 0.16-4.1 µM. Representative dose-response curves in A549 cells are shown in FIG. 3A, which indicate that compounds 4 and 7 had greater potencies than compounds 3, 6, and 9. Dose-response curves were used for calculating the IC$_{50}$ values in the entire NSCLC panel, and are shown in FIGS. 3B-F. These IC$_{50}$ values showed that compound 4 (IC$_{50}$: 0.12-0.31 µM) and compound 7 (IC$_{50}$: 0.14-0.29 µM) had greater potencies (at least 10-fold) than compound 3 (IC$_{50}$: 2.4-4.1 µM), compound 6 (IC$_{50}$: 1.5-2.8 µM), and compound 9 (IC$_{50}$: 2.1-3.9 µM) in all NSCLC cell lines. Clearly, the structural differences affected the potency of the molecules. Moreover, these results indicated that the IC$_{50}$ values in WT-p53 models were similar to those in Mut- and Null-p53 cell lines. To confirm that sensitivity to gold compounds was not dependent on p53 status, the Applicant utilized WT-p53 A2780 ovarian cancer cells in which p53 was knocked out using the CRISPR/Cas9 technology (CRISPR p53 KO). The corresponding control cells were transfected with a control plasmid and retained WT-p53 status. Results from the MTT assay revealed there were no significant differences in IC$_{50}$ for compound 3 (CRISPR Control, 0.87±0.11 µM vs. CRISPR p53 KO, 1.13±0.39 µM) and compound 4 (CRISPR Control, 0.087±0.003 µM vs. CRISPR p53 KO, 0.083±0.003 µM) (see FIG. 4). The cytotoxicity of gold compounds was independent of p53 status. The results also indicate the consistent difference in the potency (e.g., IC$_{50}$) between different compounds. However, higher potencies may not be an indicator of success at the clinical level, and this was well demonstrated by the ~10-fold difference in potency between cisplatin and the equally potent carboplatin (Kelland, L. R.; Murrer, B. A.; Abel, G. Giandomenico, C. M.; Mistry, P.; Harrap, K. R. Ammine/Amine Platinum(IV) Dicarboxylates: A Novel Class of Platinum Complex Exhibiting Selective Cytotoxicity to Intrinsically Cisplatin-resistant Human Ovarian Carcinoma Cell Lines. Cancer Res. 1992, 15; 52(4), 822-8, incorporated herein by reference in its entirety). Thus, other factors have to be taken into consideration to assess the clinical potential of new agents, such as toxicity.

Cisplatin resistance is a critical factor that limits the clinical utility of cisplatin; therefore, identification of agents that do not depend on wild-type p53 status for antitumor response is an important goal as both NSCLC and ovarian cancer patients with p53 mutation have shorter overall survival and shorter time to progression (Galluzzi, L.; Vitale, I.; Michels, J.; Brenner, C.; Szabadkai, G.; Harel-Bellan, A.; Castedo, M.; Kroemer, G. Systems biology of cisplatin resistance: past, present and future. Cell Death Dis. 2014, 29; 5, e1257; Siddik, Z. H. Cisplatin: mode of cytotoxic action and molecular basis of resistance. Oncogene. 2003, 22, 7265-7279; Stewart, D. J. Mechanisms of resistance to cisplatin and carboplatin. Crit Rev. Oncol Hematol. 2007, 63(1), 12-31; Ahrendt, S. A.; Hu, Y.; Buta, M.; McDermott, M. P.; Benoit, N.; Yang, S. C., Wu, L.; Sidransky, D. p53 Mutations and Survival in Stage 1 Non-Small-Cell Lung Cancer: Results of a Prospective Study. J. Natl. Cancer Inst. 2003, 95(13), 961-70; and Reles, A.; Wen, W. H.; Schmider, A.; Gee, C.; Runnebaum, I. B.; Kilian, U.; Jones, L. A.; El-Naggar, A.; Minguillon, C.; Schönborn, I.; Reich O.; Kreienberg, R.; Lichtenegger, W.; Press, M. F. Correlation of p53 Mutations with Resistance to Platinum-based Chemotherapy and Shortened Survival in Ovarian Cancer. Clin. Cancer Res. 2001, 7(10), 2984-97, each incorporated herein by reference in their entirety). The fundamental mechanism of cisplatin resistance is the failure of this drug to activate p53, even in tumor cells primed for wild-type p53 function (Fritsche, M.; Haessler, C.; Brandner, G. Induction of nuclear accumulation of the tumor-suppressor protein p53 by DNA-damaging agents. Oncogene. 1993, 8(2), 307-18; and Shich, S. Y.; Ikeda, M.; Taya, Y.; Prives C. DNA Damage-Induced Phosphorylation of p53 Alleviates Inhibition by MDM2. Cell. 1997, 91(3), 325-34, each incorporated herein by reference in their entirety).

Thus the potential of the gold compounds to circumvent this resistance was investigated. For this purpose the IC$_{50}$ and fold resistance (A2780cis/A2780) values for selected gold compounds were determined using the sensitive A2780 cancer cell line and the corresponding cisplatin-resistant A2780cis and 2780CP-16 cell lines.

While the A2780cis (cisplatin-resistant) cells showed an IC$_{50}$ for cisplatin about 7-fold higher than A2780 (cisplatin-sensitive) cells, the IC$_{50}$ of the most active compounds 1, 2, 4, 5, 7, and 8 resulted in similar or lower values in A2780cis with respect to A2780 (fold resistance or resistant factor less than 1) (Table 2). Similar results were obtained also in the 20-fold cisplatin-resistant 2780CP cells (data not shown), indicating that gold compounds disclosed herein may have the ability to overcome cisplatin-resistance to a substantial extent.

Example 5 Evaluation of Apoptosis and ROS Formation

PC3 (2.5×10$^4$), MCF-7 (5.0×10), A2780 and A2780cis (5.0×10), and L-540 cells (2.0×10$^5$/mL) were incubated in six-well plates with compound 1 at $IC_{75}$ (see FIGS. 1A-IV) for 72 h. Annexin-V binding (Becton-Dickinson [BD] Pharmingen, San Jose, Calif.) together with propidium iodide (PI) staining was detected in tumor cells by flow cytometry, as described. Caspase 3 activation was evaluated using the fluorochrome inhibitors of caspases (FLICA) Caspa-Tag™ caspase-3/7 (FAM-DEVD-FMK) (Chemicon International, Milan, Italy). Briefly, cells were treated with compound 1 at $IC_{75}$ for 0 hours, 48 hours, and 96 hours, then harvested, washed, and resuspended in warmed complete medium supplemented with FLICA for 1 h and then immediately analyzed by flow cytometry. DNA fragmentation was assessed using the Apo-Direct kit (Becton-Dickinson Pharmigen, CA, USA) according to manufacturer's instructions. For mitochondrial ROS evaluation, cells treated with compound 1 were incubated with 5 µM of MitoSox reagent working solution (Molecular Probes, Invitrogen) for 30 minutes at 37° C. Red fluorescence was immediately analyzed by flow cytometry. Viable cells were identified according to their forward and right-angle scattering, electronically gated and analyzed on a FACScan flow cytometer (BD), using CellQuest software (BD). In another series of experiments, cells were exposed to compound 1 at $IC_{75}$ in the presence or absence of the antioxidant and ROS scavenger N-acetyl-cysteine (NAC; 5 mM) (Sigma). After 72 h, ROS formation and viable cells number were evaluated by flow cytometry and trypan blue dye exclusion assay, respectively.

Figure 1B:
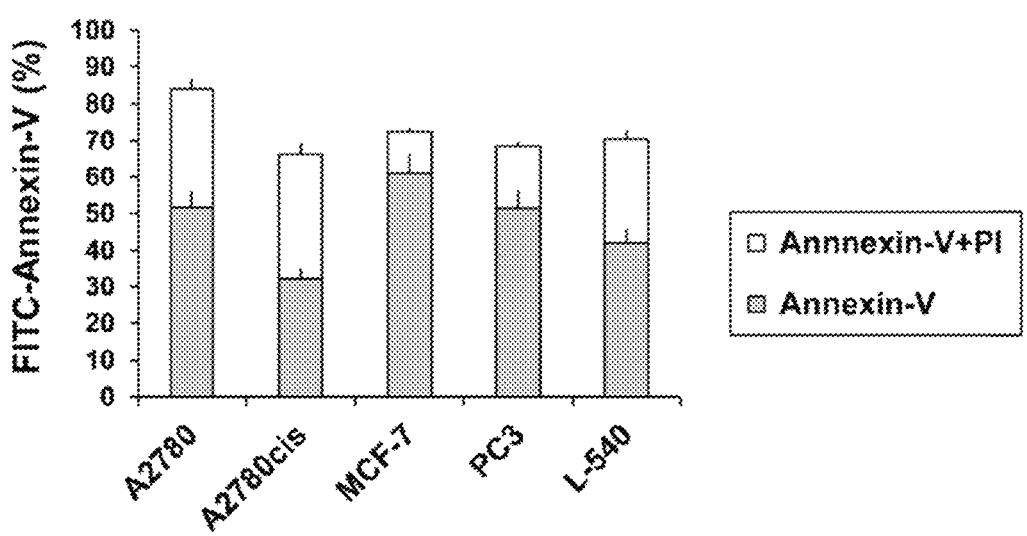
FIG. 1B shows the fluorescence-activated cell sorting (FACS) analysis of cells after 72 h incubation with compound 1 at $IC_{75}$ and doubly stained with Annexin V/FITC and PI.

There may be several mechanisms involved in the anticancer activity of gold(I) and gold(III) compounds including the capability of inducing apoptosis (Nardon, C.; Boscutti, G.; Fregona, D. Beyond platinums: gold complexes as anticancer agents. *Anticancer Res.* 2014, 34(1), 487-492, incorporated herein by reference in its entirety). Therefore the Applicant tested the capability of the most active compound 1 to inhibit human tumor cell proliferation by inducing apoptosis using the Annexin-V/PI double staining assay, caspase 3 activation and DNA fragmentation (see FIGS. 1A-1V). The Applicant analyzed apoptosis by Annexin-V/PI staining in tumor cells after treatment for 72 h with an $IC_{75}$ dose of compound 1. As shown in FIG. 1B, compound 1 induced apoptosis in all cell lines tested and the results represented the mean±SEM of three independent experiments. Treatment with compound 1 resulted in a substantial phosphotidylserine exposure (Annexin-V) together with a high percentage of cells permeable to PI staining, thus supporting apoptosis as a major mechanism of cell death (see FIG. 1B). Consistently, treatment with compound 1 at $IC_{75}$ induced a time-dependent activation of caspase 3 (see FIGS. 1C-IQ). The dotted lines indicate the background fluorescence of cells (medium). The x- and y-axes indicate the logarithms of the relative fluorescence intensity and relative cell number, respectively. The FACS analysis/histograms were representative of one of three different experiments. Apoptosis induction was confirmed by DNA fragmentation (see FIGS. 1R-1V) with Apo-Direct analysis. Compound 1 was active at the same concentration in both cisplatin-sensitive (A2780) and cisplatin-resistant (A2780cis) ovarian cancer cells (see FIGS. 1A-1V).

Taken together, these results showed that compound 1 induced apoptosis in all cell lines tested, suggesting that the observed growth inhibition was due to apoptosis induction and that it was capable of overcoming resistance to cisplatin.

Figure 2A:
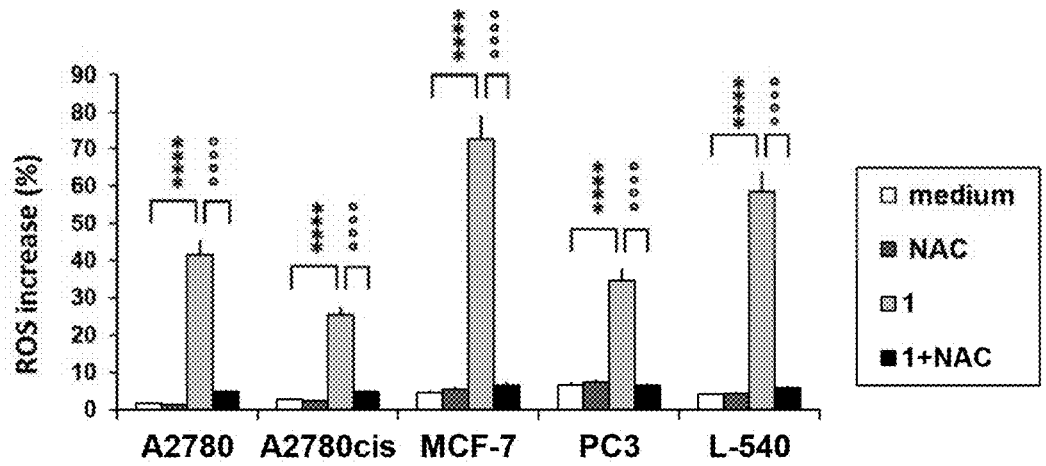
FIG. 2A shows the percentage of ROS positive cells after the treatment with compound 1 at $IC_{75}$ for 72 hours in the presence or absence of the antioxidant NAC (5 mM).

Gold(I) and gold(III) compounds were shown to inhibit the activity of the selenoenzyme TrxR and to promote ROS production, suggesting a potential major involvement of a deregulation of the TrxR redox system in their antiproliferative activity (Muhammad. N.; Guo, Z. Metal-based anticancer chemotherapeutic agents. *Curr Opin Chem Biol.* 2014, 19, 144-53, incorporated herein by reference in its entirety). Therefore, the Applicant assessed the capability of compound 1 of inducing ROS accumulation and of decreasing TrxR enzymatic activity. As shown in FIG. 2A, treatment with compound 1 at IC s increased mitochondrial ROS, as evaluated by Mitosox Red assay in all cell lines tested and especially in breast cancer MCF-7 cells.

Figure 2B:
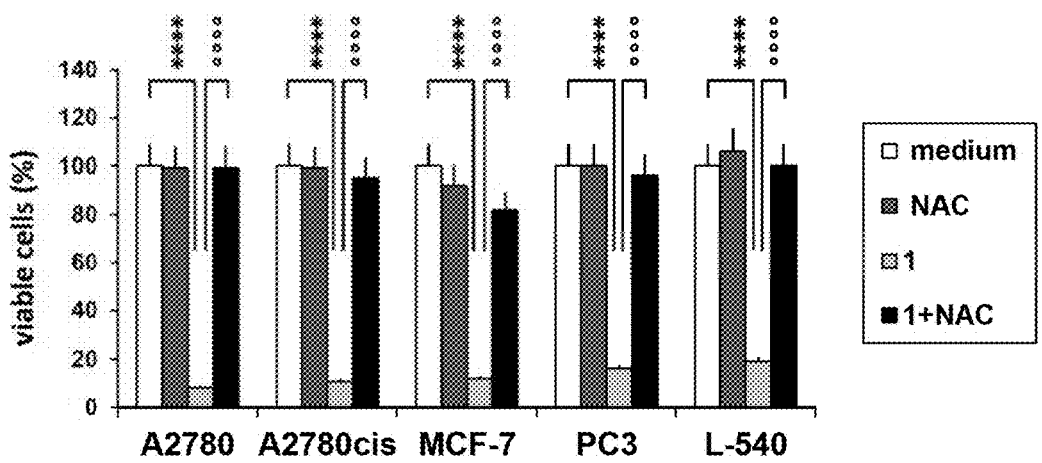
FIG. 2B shows the percentage of viable cells after the treatment with compound 1 at $IC_{75}$ for 72 hours in the presence or absence of the antioxidant NAC (5 mM).

In order to establish a possible relationship between ROS overproduction and decreased cell viability, tumor cells were incubated with the ROS scavenger NAC before compound 1 treatment (FIGS. 2A and 2B). In FIGS. 2A and 2B, the values represent the mean±SEM of three different experiments, "****" means $p<0.0001$ for compound 1 vs control, and "°°°°" means $p<0.0001$ for compound 1 vs compound 1+NAC. NAC blocked ROS production (see FIG. 2A) and almost completely neutralized the anti-proliferative effect of compound 1 (see FIG. 2B), thus suggesting that the cytotoxic activity may be due to ROS generation. However, the Applicant cannot exclude that thiol-containing antioxidant NAC could block the effects of compound 1 by binding with the active site of the gold compound, as demonstrated for other gold compounds.

Example 6 Thioredoxin Reductase (TrxR) and Proteasome Enzymatic Activity Assays

A2780, A2780cis, MCF-7 and PC3 cells ($5.0 \times 10^5$) and L-540 cells ($2.0 \times 10^5$/mL) were treated for 72 h with increasing concentrations of compound 1. TrxR (EC 0.8.1.9) activity in cultured cells was assessed using the TrxR Assay Kit (Sigma-Aldrich), according to the manufacturer's instructions. Cells were lysed with lysis buffer (50 mM Tris-HCl, 0.1% Triton X-100, 0.9% NaCl, pH 7.6) on ice for 30 min. Cell lysates were then incubated in 100 mM of potassium phosphate with 10 mM ethylenediaminetetracetic acid (EDTA) and 0.24 mM nicotinamide adenine dinucleotide phosphate (NADPH) with and without a TrxR inhibitor. The reaction was started by adding dinitrothiocyanobenzene (DNTB) and it was monitored spectrophotometrically at 412 nm. Proteasome activity (EC 3.4.25.1) was assayed in cytosolic extracts using the 20S Proteasome Activity Assay kit (Chemicon International, Milano, Italy) accordingly to manufacturer's instructions. The assay was based on the detection of the fluorophore 7-amino-4-methylcoumarin (AMC) after cleavage from the labeled substrate LLVY-AMC. Levels of released AMC were measured using an excitation wavelength of 380 nm and an emission wavelength of 460 nm with an automatic multiwell plate reader. The relative activity was standardized by protein concentration, determined using the protein assay dye reagent (Bio-Rad Laboratories).

Figure 2C:
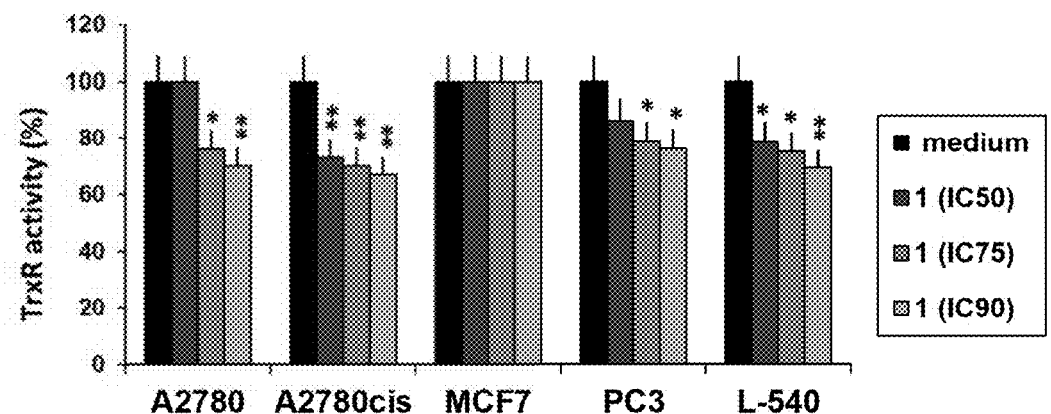
FIG. 2C shows the inhibition of TrxR enzymatic activity in cells treated with compound 1 at $IC_{50}$, $IC_{75}$, and $IC_{90}$ for 72 hours.

Since TrxR was involved in the maintenance of intracellular redox balance, ROS detoxification and inhibition of pro-apoptotic molecules, the Applicant also investigated the effects of compound 1 on the enzymatic activity of TrxR (Liu, Y.; Li, Y.; Yu, S.; Zhao, G. Recent advances in the development of thioredoxin reductase inhibitors as anticancer agents. Curr. Drug Targets. 2012, 13, 1432-1444, incorporated herein by reference in its entirety). As shown in FIG. 2C, compound 1 showed a dose-dependent inhibition of TrxR enzymatic activity in most cell lines except for MCF-7 cells, which remained unaffected at the highest drug concentration at $IC_{90}$. In FIG. 2C, the values represent the mean±SEM of three different experiments, "*" means $p<0.05$, and "**" means $p<0.01$.

The TrxR enzymatic activity was evaluated by a thioredoxin reductase assay kit. However, TrxR activity was reduced by compound 1 by no more than 30% with respect to the control (see FIG. 2C) at a high concentration of compound 1, suggesting that TrxR activity was not the main target of compound 1.

The proteasome represents a crucial component of the protein quality control system and its inhibition leads to the accumulation of un-degraded proteins that are potentially toxic, thus suggesting specific proteasome inhibitors as anticancer agents (Baumann, K. How the proteasome adapts to stress. *Nat. Rev. Mol. Cell Biol.* 2014, 15(9), 562-3, incorporated herein by reference in its entirety). Since gold(III) compounds were shown to inhibit the proteasome activity in cancer cells, the Applicant evaluated its activity with a proteasome assay kit after the cells were treated with compound 1.

Figure 2D:
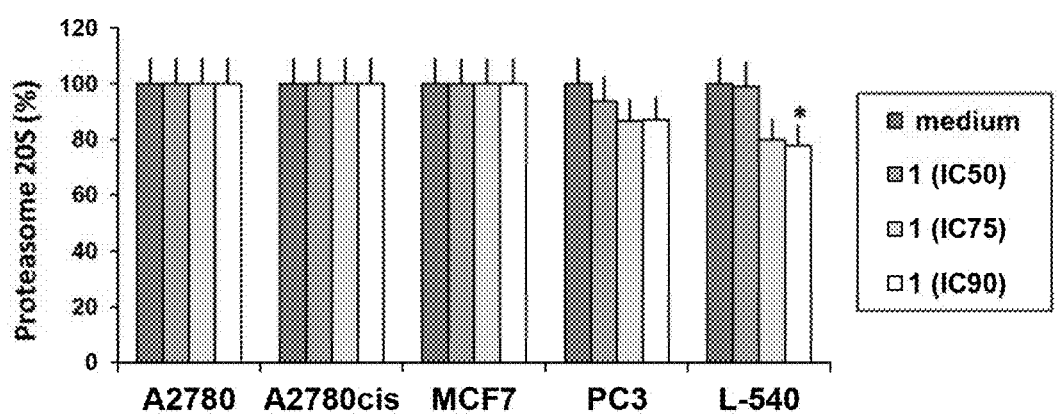
FIG. 2D shows the inhibition of proteasome's chymotrypsin-like activity in cells treated with compound 1 at $IC_{50}$, $IC_{75}$, and $IC_{90}$ for 72 hours.

As shown in FIG. 2D, compound 1 slightly reduced the 20S proteasome activity in L-540 cells (about 20% of control) and was un-effective in all the other cell lines tested. In FIG. 2D, the values represent the mean±SEM of three different experiments, and "*" means p<0.05.

However, the Applicant cannot exclude that the other active compounds (i.e., compounds 2, 4, 5, 7, and 8) may affect TrxR or the proteasome activity. Further experiments to discover the mechanism of the cytotoxic activity of these new gold(III) compounds are needed to fully appreciate the mode of action of these agents.

Drug resistance to chemotherapeutic agents is a central problem in oncology. The gold(III) compounds disclosed herein were effective in cisplatin-resistant, as well as in p53-defective cancers cells of different tumor types. Moreover, the disclosed compounds contain a dithiocarbamate group capable of preventing a reaction with other sulfur-containing proteins, and thus the Applicant hypothesized these compounds may lead to a reduced toxicity in vivo.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A gold(III) complex selected from the following:

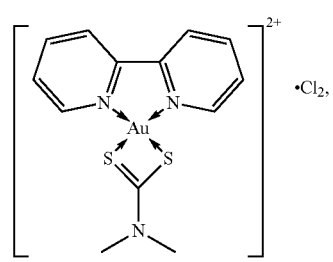

-continued

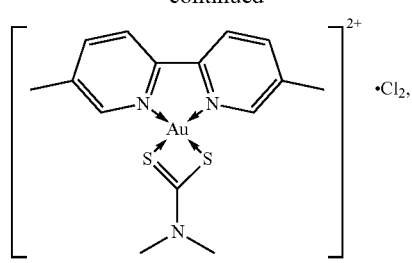

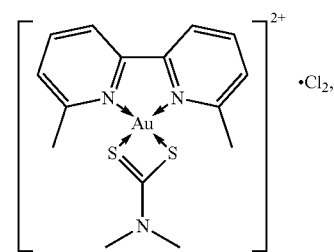

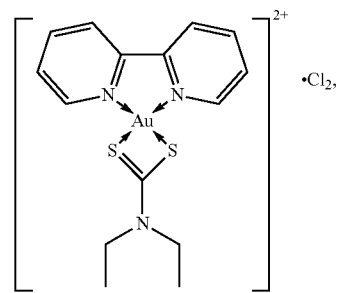

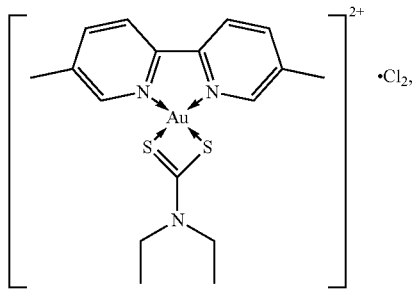

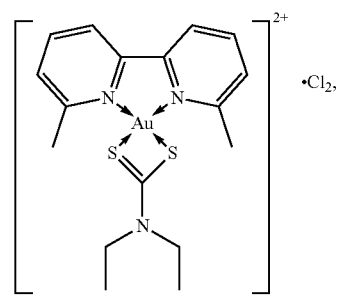

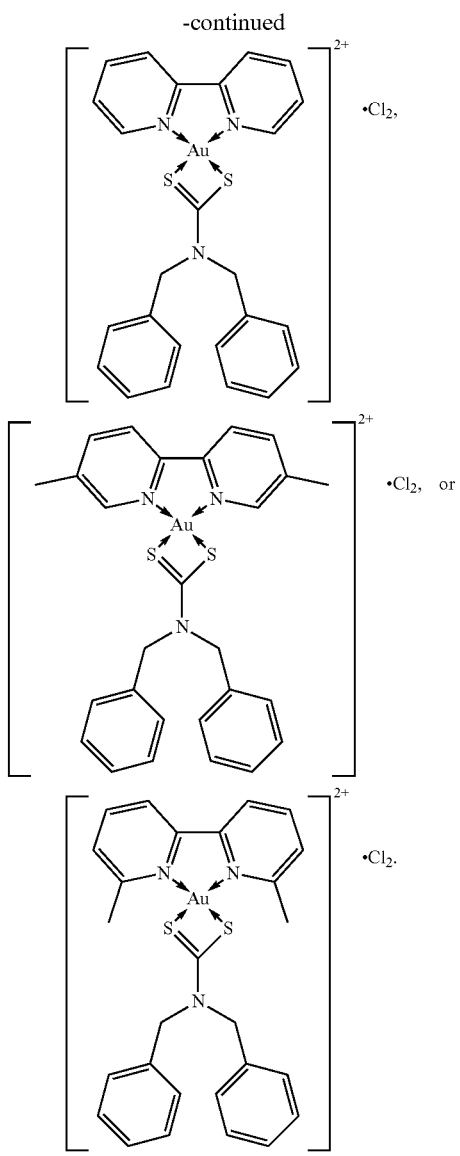

2. A pharmaceutical composition, comprising:
the gold(III) complex of claim 1; and
at least one pharmaceutically acceptable carrier and/or excipient.

3. The pharmaceutical composition of claim 2, wherein the at least one pharmaceutically acceptable carrier and/or excipient is selected from the group consisting of water, an organic solvent, an animal fat, a vegetable fat, a vegetable oil, and a polymer.

4. The pharmaceutical composition of claim 2, wherein the pharmaceutical composition comprises 0.1-10 wt % of the gold(III) complex, based on a total weight of the pharmaceutical composition.

5. A method for treating cancer, comprising: administering an effective amount of the gold(III) complex of claim 1 to a subject in need thereof, wherein the cancer is selected from the group consisting of prostate cancer, lung cancer, breast cancer, ovarian cancer, and Hodgkin lymphoma.

6. The method of claim 5, wherein the effective amount is in a range of 1-100 mg/kg body weight of the subject.

7. The method of claim 5, wherein the cancer is at least one selected from the group consisting of prostate cancer, lung cancer, breast cancer, ovarian cancer, and Hodgkin lymphoma.

8. The method of claim 5, wherein the cancer is prostate cancer which is resistant to androgen deprivation therapy.

9. The method of claim 5, wherein the cancer is resistant to at least one platinum-based chemotherapy drug.

10. The method of claim 9, wherein the cancer is ovarian cancer.

11. A method for inhibiting growth of cancer cells, comprising: contacting a cytotoxic amount of the gold(III) complex of claim 1 with the cancer cells, wherein the cancer cells are selected from the group consisting of prostate cancer, lung cancer, breast cancer, ovarian cancer, and Hodgkin lymphoma cells.

12. The method of claim 11, wherein the cancer cells are from at least one cell line selected from the group consisting of PC3, MCF-7, A2780, A2780cis, A2780CP-16, H460, A549, H226, H838, H157, H1975, H2122, SKLU1, H1299, and L-540.

* * * * *